United States Patent [19]
Kuzuya et al.

[11] Patent Number: 5,858,645
[45] Date of Patent: Jan. 12, 1999

[54] ASSAY UTILIZING HYDROGEN PEROXIDE ADDUCT

[75] Inventors: Keiko Kuzuya; Tadakazu Yamauchi, both of Tokyo, Japan

[73] Assignee: Mochida Pharmaceutical Co., Ltd., Tokyo, Japan

[21] Appl. No.: 773,181

[22] Filed: Dec. 27, 1996

[30] Foreign Application Priority Data

Dec. 28, 1995 [JP] Japan ................................. 7-343822

[51] Int. Cl.$^6$ ..................................................... C12Q 1/28
[52] U.S. Cl. ..................................... 435/4; 435/6; 435/71; 435/72; 435/7.91; 435/7.92; 435/7.93; 435/7.94; 435/28
[58] Field of Search ......................... 435/283.1, 4, 6, 435/7.1, 7.2, 7.91, 7.92, 7.93, 7.94, 28

[56] References Cited

U.S. PATENT DOCUMENTS

| | | | |
|---|---|---|---|
| 5,098,830 | 3/1992 | Bar-or | 435/28 |
| 5,516,644 | 5/1996 | Yamauchi et al. | 435/7.9 |

FOREIGN PATENT DOCUMENTS

| | | |
|---|---|---|
| 085261A1 | 8/1983 | European Pat. Off. . |
| 0525723 | 2/1993 | European Pat. Off. . |
| 0663446 | 7/1995 | European Pat. Off. . |
| 663446A2 | 7/1995 | European Pat. Off. . |
| 0690306 | 1/1996 | European Pat. Off. . |
| 5-264552 | 10/1993 | Japan . |
| 7-234201 | 9/1995 | Japan . |
| 8-75748 | 3/1996 | Japan . |
| 185318 | 7/1987 | United Kingdom . |
| WO8502018A1 | 5/1985 | WIPO . |

*Primary Examiner*—Ponnathapura Achutamurthy
*Attorney, Agent, or Firm*—Birch, Stewart, Kolasch & Birch, LLP

[57] ABSTRACT

Improvement in assays utilizing at least hydrogen peroxide for one analysis reagent is provided. The assay of the present invention employs a stable hydrogen peroxide adduct in dry state which has no adverse effects on the assay, and which has a high hydrogen peroxide-retaining ability. In the assay, an aqueous solution is added to an adduct in dry state of (a) at least one member selected from the group consisting of a carboxylic acid and a salt thereof, phosphoric acid and a salt thereof, and a sulfonic acid and a salt thereof, and (b) hydrogen peroxide to generate peroxide, and the thus generated peroxide is used for the analysis reagent.

17 Claims, 17 Drawing Sheets

ASSAY UTILIZING HYDROGEN PEROXIDE ADDUCT

BACKGROUND OF THE INVENTION

This invention relates to an assay wherein hydrogen peroxide is used as an assay reagent, and wherein hydrogen peroxide in a stable, dry hydrogen peroxide adduct form is used without inducing any adverse effects on the assay principle.

Typical assays wherein peroxide is used as an assay reagent are chemiluminescence assays. For example, in a chemiluminescence reaction known as peroxalate chemiluminescence, a high energy intermediate is generated from an oxalic acid derivative and hydrogen peroxide in the presence of a basic catalyst, and a fluorescent reagent is excited by the resulting energy to thereby induce luminescence. In the case of a luminol derivative, it is oxidized by hydrogen peroxide in the presence of $Fe(CN)_6^{3-}$, microperoxidase, or peroxidase to result in the excited state of aminophthalic acid, and the luminescence occurs upon returning of the excited aminophthalic acid to its ground state. An acridinium derivative also undergoes luminescence with the addition of hydrogen peroxide. Such chemiluminescence reactions are widely used in various assays including those based on a specific binding reaction, and in such assays, the luminescence compound or the catalyst (such as enzyme) for the luminescence reaction is incorporated as a label. Hydrogen peroxide is also incorporated in such assay as a reagent indispensable for inducing the luminescence. The chemiluminescence reactions as described above exhibit a relatively high sensitivity, and therefore, these reactions are widely employed for the assays in various fields including clinical tests and environmental tests.

The assays wherein hydrogen peroxide is used as an assay reagent are not limited to the chemiluminescence assays. Peroxidase enzymes such as horseradish peroxidase (hereinafter referred to as HRPO) and microperoxidase are also used for the catalyst of color development reactions and electrochemical reactions. HRPO is used for the labeling enzyme in many assays including enzyme immunoassays, nucleic acid hybridization assays, and immunohistostaining assays wherein a tissue or cells are stained with a labeled antibody specific therefor, and in such assays, hydrogen peroxide, which is the substrate for the HRPO, is used as an assay reagent. Hydrogen peroxide is also used in occult blood test of feces wherein peroxidase activity of hemoglobin in feces is detected by color development reaction and hydrogen peroxide is added as the substrate of the enzymatic reaction. Other catalysts having peroxidase activity include ions and cheletes of a metal, porphyrin derivatives, catalyst antibodies, and the like, and these catalysts are also used in various assays wherein peroxide is used as an assay reagent as in the case of the enzyme catalysts as described above.

Recently, MEDIA (mediator diffusion-controlled immunoassay) has been disclosed as a specific binding assay wherein a signal substance generator such as an enzyme is used for the labeling agent to be developed through the matrix with the liquid sample; and the labeling agent is allowed to form a distribution of a particular profile in terms of the distance of the labeling agent from the detection port by the specific binding reaction between the analyte in the liquid sample and the specific binding substance; and the current corresponding to the analyte concentration of the liquid sample which is controlled by diffusion of the signal substance such as an electron mediator generated from the labeling agent is measured to thereby determine the concentration of the analyte. (See Japanese Patent Application Laid-Open No. 5(1993)-264552(EP 0 525 723 A2) and Japanese Patent Application Laid-Open No. 7(1995)-234201.) In MEDIA, HRPO is again used for the labeling agent in view of its high sensitivity as an oxidoreductase, and hydrogen peroxide is used in combination with the HRPO as the substrate for the label enzyme HRPO.

In the wide variety of assays as described above, the principle that a reaction specific for the analyte is detected by utilizing hydrogen peroxide has been adopted as would be appreciated from the foregoing description. A process capable of providing the hydrogen peroxide in stable, dry state without inducing any adverse effect on the assay principle is urgently required both for the convenience of the assay procedure and for the stability of the assay reagent.

Conventional means of retaining the hydrogen peroxide in dry state include dried urea-hydrogen peroxide adduct (Hyperole) and dried sodium carbonate-hydrogen peroxide adduct. These adducts are used in other fields as a bleach, a cleaner, a hair dye, and the like. The hydrogen peroxide adducts with urea and sodium carbonate are highly moisture absorptive and unstable, and could not endure long-term storage. Furthermore, urea is a compound which is well known as a denaturing agent of proteins, and accordingly, suffered from the defects that its use resulted in adverse effects when used in the assays as described above wherein proteins were involved as the analyte or assay reagents. Sodium carbonate also suffered from the detect of the high pH after its dissolution, and such defect inhibited its use in the assay purposes.

The MEDIA (mediator diffusion-controlled immunoassay) as described above is a specific binding assay provided with the feature of a dry chemistry assay wherein no washing operation is required and the assay can be conducted by merely adding the liquid sample to the assay device. In the MEDIA device described in Japanese Patent Application Laid-Open No. 7(1995)-234201, hydrogen peroxide in dry state was incorporated in the assay device in the form of urea-hydrogen peroxide adduct. In this device, however, the urea-hydrogen peroxide adduct in dry state had to be located at the downstream end of the assay device to prevent the adverse influence of urea on the antigen-antibody reaction and the enzyme reaction. Due to such remote location of the urea from the reaction site, a considerable time period was required for the establishment of stable response and quick measurement could not be realized in spite of the various measures taken for the promotion of natural diffusion of the hydrogen peroxide back to the reaction site. In addition, despite such remote location of the urea-hydrogen peroxide adduct from the reaction site, the assay device still suffered from inhibitory effects on the specific reaction of the urea that reversely diffused along the flow path after a while.

SUMMARY OF THE INVENTION

An object of the present invention is to provide an improvement in the assay and the assay device utilizing hydrogen peroxide as an assay reagent. More illustratively, the object of the present invention is to provide the assay and the assay device wherein a stable hydrogen peroxide adduct in dry state having a high hydrogen peroxide-retaining ability is used with inducing little adverse effect on the assay principle.

In view of the situation as described above, the inventors of the present invention made an extensive study, and found that a hydrogen peroxide adduct in dry state containing at least one member selected from the group consisting of a carboxylic acid and a salt thereof, phosphoric acid and a salt thereof, and a sulfonic acid and a salt thereof has little adverse effect on the assay reaction as well as a high hydrogen peroxide-retaining ability. The present invention has been completed on such finding. The inventors of the present invention also found that it is also preferable to use monosaccharides, disaccharides, sugar alcohols, polymers thereof, N-acetylglucosamine, ascorbic acid, creatinine and polyethylene glycol which are free from either of carboxyl group, phosphono group or sulfo group instead of the acids and the salts thereof as mentioned above.

According to the present invention there is provided an assay utilizing at least peroxide for one analysis reagent wherein an aqueous solution is added in the course of the assay to an adduct in dry state of (a) at least one member selected from the group consisting of a carboxylic acid and a salt thereof, phosphoric acid and a salt thereof, and a sulfonic acid and a salt thereof, and (b) hydrogen peroxide to generate peroxide, the thus generated peroxide being used for the analysis reagent.

According to the present invention, there is also provided an assay wherein an analyte is qualitatively or quantitatively detected in an assay device provided at least with a flow path and a detection means by the assay utilizing at least peroxide for one analysis reagent; and wherein said adduct in dry state of (a) at least one member selected from the group consisting of a carboxylic acid and a salt thereof, phosphoric acid and a salt thereof, and a sulfonic acid and a salt thereof, and (b) hydrogen peroxide is arranged at any site within said assay device such that the assay is commenced by introducing the aqueous solution in the assay device to generate peroxide and the thus generated peroxide is utilized for the qualitative or quantitative detection of the analyte.

Preferably, the assay is an assay wherein an analyte is detected by using a catalyst having peroxidase activity, and wherein said aqueous solution is introduced in the course of the assay to generate peroxide which is to be involved in the catalytic reaction.

The component (a) is preferably at least one member selected from the group consisting of monocarboxylic acids represented by the following formula (1):

$$\begin{array}{c} COOH \\ | \\ R^2-C-R^1 \\ | \\ R^3 \end{array} \quad (1)$$

wherein $R^1$: H or $-CH_2-OH$
$R^2$: H, $-NH_2$, $-OH$, or $-CH_2-OH$
$R^3$: H, $-CH_3$, $-CH(OH)-CH_3$, $-C_6H_4-OH$, $-(CH_2)_w-OH$ (W = 1–3), $-(CH(OH))_x-CH_2-OH$ (X = 1–5), $-(CH_2)_y-NH-CO-NH_2$ (y = 0–3), or $-(CH_2)_z-NH-CO-CH_3$ (z = 0–3)

pyruvic acid, and sodium and potassium salts thereof.

It is also preferable that the component (a) is at least one member selected from the group consisting of an aliphatic dicarboxylic acid, an aromatic dicarboxylic acid, and sodium and potassium salts thereof.

It is also preferable that the component (a) is at least one member selected from the group consisting of tricarboxylic acids represented by the following formula (2):

$$\begin{array}{c} R^4 \\ | \\ COOH-(CH_2)_p-C-(CH_2)_q-COOH \\ | \\ (CH_2)_r \\ | \\ COOH \end{array} \quad (2)$$

wherein $R^4$ is H or $-OH$, and p is from 1 to 3, q is from 0 to 3, and r is from 0 to 3; and formula (3):

$$\begin{array}{c} R^5 \quad COOH \\ \diagdown \diagup \\ C \\ \| \\ C \\ \diagup \diagdown \\ HOOC \quad (CH_2)_s-COOH \end{array} \quad (3)$$

wherein $R^5$ is H or $CH_3$, and s is from 1 to 3; and sodium and potassium salts thereof.

It is also preferable that the component (a) is at least one member selected from the group consisting of tetracarboxylic acids represented by the following formula (4):

$$\begin{array}{c} COOH \quad COOH \\ | \quad\quad | \\ COOH-(CH_2)_t-CH-(CH_2)_u-CH-(CH_2)_v-COOH \end{array} \quad (4)$$

wherein t is from 0 to 3, u is from 0 to 3, and v is from 0 to 3; and
sodium and potassium salts thereof.

It is also preferable that the component (a) is at least one member selected from the group consisting of a uronic acid, a polyuronic acid, and sodium and potassium salts thereof.

It is also preferable that the component (a) is at least one member selected from the group consisting of a hydroxy-alkanesulfonic acid, aminoalkanesulfonic acid, hydroxybenzenesulfonic acid, and sodium and potassium salts thereof.

It is also preferable that the component (a) is at least one member selected from phosphoric acid, and sodium and potassium salts thereof.

According to the present invention, there is also provided an assay utilizing at least peroxide for one analysis reagent wherein an aqueous solution is added in the course of the assay to an adduct in dry state of (a) at least one member selected from the group consisting of a monosaccharide, a disaccharide, a sugar alcohol, and polymers thereof, and (b) hydrogen peroxide to generate peroxide, the thus generated peroxide being used for the analysis reagent.

According to the present invention, there is also provided an assay utilizing at least peroxide for one analysis reagent wherein an aqueous solution is added in the course of the assay to an adduct in dry state of (a) at least one member selected from the group consisting of a N-acetylglucosamine, ascorbic acid, creatinine, and polyethylene glycol, and (b) hydrogen peroxide to generate peroxide, the thus generated peroxide being used for the analysis reagent.

According to the present invention, there is also provided assay utilizing at least peroxide for one analysis reagent conducted in an assay device provided at least with a flow path and a detection means, wherein an aqueous solution is added in the course of the assay to an adduct in dry state of (a) at least one member selected from the group consisting of carboxyl group, phosphono group, sulfo group, and salts thereof of a solid substance present in the flow path, and (b) hydrogen peroxide to generate peroxide, the thus generated peroxide being used for the analysis reagent.

DETAILED DESCRIPTION OF THE INVENTION

Figure 1:
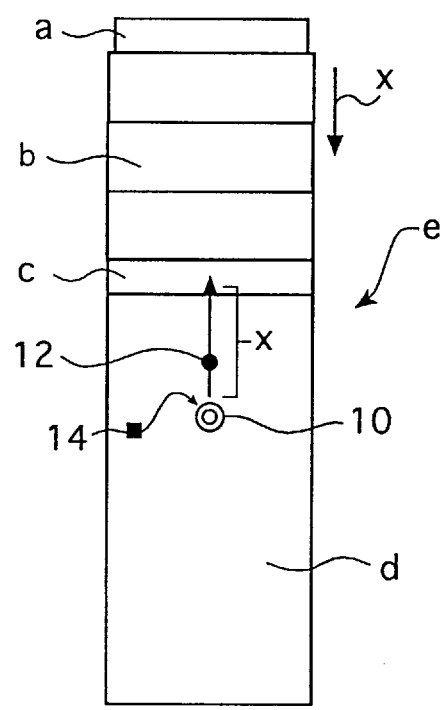
FIG. 1 is a schematic view showing the principle of an embodiment of the specific binding assay (MEDIA) device utilizing the assay process of the present invention.

Next, the assay of the present invention is described in detail.

Assay principle of the present invention is not limited to any particular type so long as peroxide, illustratively hydrogen peroxide, is used for an analysis reagent, and the analyte is qualitatively or quantitatively detected. Exemplary such assays include the following types of assays.

(1) Assays wherein catalytic activity (e.g. peroxidase activity and catalase activity) of the analyte in the sample is detected by using hydrogen peroxide as an assay reagent.

For example, in the assay for detecting occult blood in feces, assay for detecting catalase activity in serum, luminol test, and the like, hydrogen peroxide is used for detecting enzymatic activity or catalytic activity of the sample.

(2) Assays wherein a label is used, and hydrogen peroxide is used as an analysis reagent for detecting such label.

In the assays such as specific binding analysis, histochemical staining analysis, cytochemical staining analysis, nucleic acid-amplification analysis such as PCR, nucleic acid-hybridization analysis, and the like wherein a luminescent substance or a catalytic substance is used for the label substance, and the label substance is detected for quantitative or qualitative analysis of the analyte, hydrogen peroxide is used as a reagent for quantitatively or qualitatively detecting the label substance.

(a) Analyte: Exemplary analytes include hem and porphyrins, substances having peroxidase activity or catalase activity, substances which function as an antibody molecule or an antigen such as proteins, polypeptides, glycoproteins, polysaccharides, complex glycolipids, and haptens; nucleic acids, effector molecules, receptor molecules, enzymes, inhibitor, and the like.

Typical analytes are hemoglobin, peroxidase, catalase; α-fetoprotein, carcinoembryonic antigen (CEA), CA125, CA19-9 and other tumor markers; $\beta_2$-microglobulin ($\beta_2$-m), ferritin and other proteins; estradiol ($E_2$), estriol ($E_3$), human chorionic gonadtropin (hCG), lutenizing hormone (LH), human placental lactogen (hPL) and other hormones; HBs antigen, HBs antibody, HBe antigen, HBe antibody, HBc antibody, HCV antibody, HIV antibody and other virus-associated antigens and virus-associated antibodies; various allergens and IgE antibodies specific for such allergens; narcotic drugs, medical drugs, and metabolites thereof; nucleic acids of virus and disease-associated polynucleotide sequences and the like.

(b) Chemiluminescent substance: Typical chemiluminescent substances are luminol derivatives, oxalic acid derivatives, and acridinium derivatives.

(c) Catalytic substance: Typical catalytic substances are fetal ions and chelate compounds thereof, $Fe(CN)_6^{-3}$, metal porphyrins and other metal complexes, hem, hemine, microperoxidase, peroxidase, catalase, and artificial enzymes such as catalytic antibodies having peroxidase activity or catalase activity.

Specific binding assay: A specific binding assay is an assay wherein an analyte in the sample is qualitatively or quantitatively detected by utilizing at least one specific binding reaction between the analyte and the specific binding substance which specifically binds to the analyte. Many specific binding assays are known in the art including immunoassay utilizing an antigen-antibody reaction; receptor assay utilizing a receptor; and nucleic acid probe assay utilizing hybridization between complimentary nucleotide sequences. The specific binding assay is utilized in many fields such as clinical tests because of the high specificity.

Specific binding substance: A specific binding substance is a substance which is capable of binding to a particular substance such as the analyte, namely, a substance capable of undergoing a specific binding reaction with a particular substance. Typical combinations of such particular substance and the specific binding substance which binds to such particular substance include an antigen and an antibody therefor; complimentary nucleic acid sequences; an effector molecule and a receptor molecule therefor; an enzyme and its inhibitor; an enzyme and a co-factor therefor; an enzyme and a substrate therefor; a compound having a sugar chain and a lectin; an antibody and an anti-antibody therefor; a receptor molecule and an antibody therefor; and the like. In such combinations, either substance of the combination may serve a specific binding substance for the other substance of the combination.

The specific binding substance may be chemically modified and/or bound to another component to form a complex to an extent that would not result in the loss of the specific binding activity. Exemplary combinations of such specific binding substance and the particular substance include an antibody or a polynucleotide chemically modified with biotin, and avidin; an antibody having avidin covalently bonded thereto and biotin; and the like. Alternatively, the specific binding substance may be a fusion protein of an antibody and an eyzyme, or an antibody and a receptor prepared by genetic recombination process.

Figure 2:
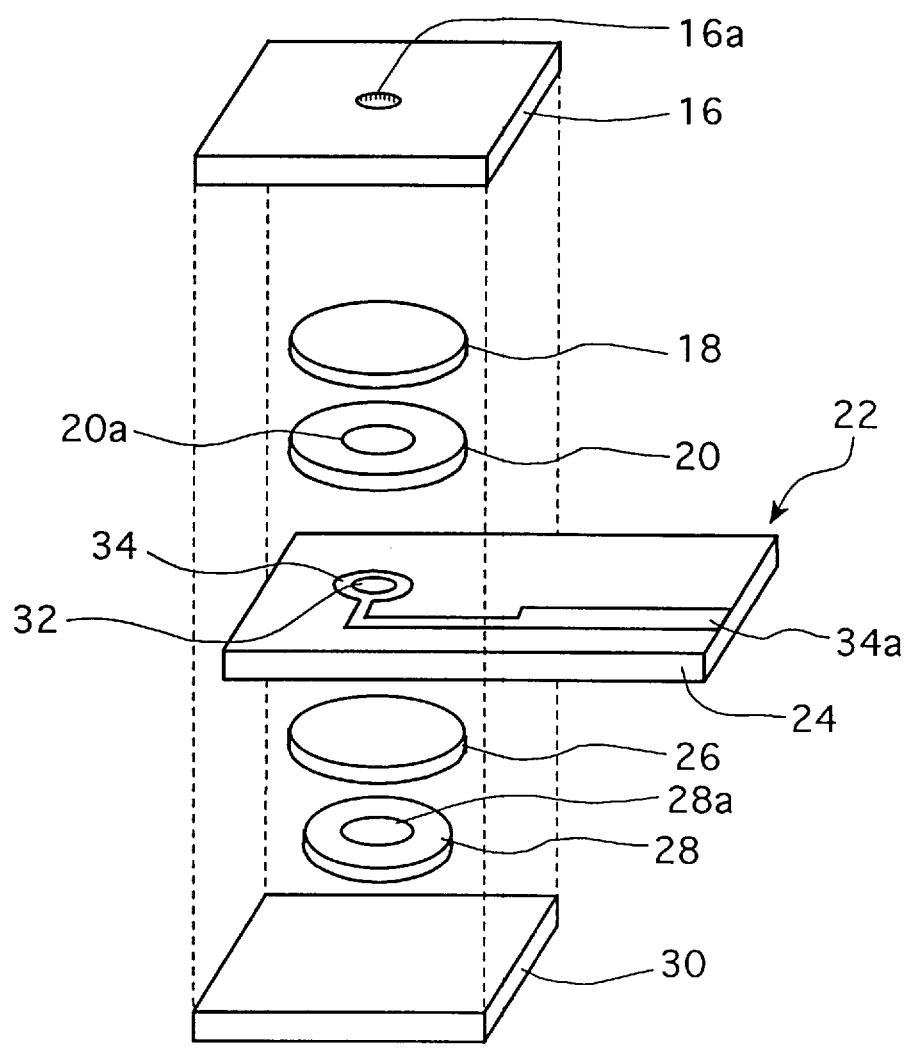
FIG. 2 is a schematic exploded perspective view of an embodiment of the specific binding assay (MEDIA) device utilizing the assay process of the present invention.

In the specification of the present invention, an embodiment wherein the present invention is used for a specific binding assay (MEDIA) is described in detail as the assay device shown in FIG. 2. In the embodiment, a substance including a moiety which functions as the specific binding substance as in the case of the signal substance generator, which will be described later, may also be referred to as a specific binding substance.

Adduct of hydrogen peroxide: An adduct of hydrogen peroxide is a peroxyhydrate; or a substance obtained after precipitating or drying a solution of the substance as described below in aqueous solution of hydrogen peroxide, or a solution prepared by adding aqueous solution of hydrogen peroxide to the solution of the substance as described below.

Flow path: A flow path is a pathway of the aqueous solution where the aqueous solution spontaneously or forcedly flow. The flow path preferably comprises a porous material or a capillary, and in such a case, the aqueous solution spontaneously wets the material.

Detection means: A detection means is the region where the signal such as color development, fluorescence, luminescence, electrochemical reaction, or the like is obtained for the assay using at least peroxide, illustratively hydrogen peroxide and the like.

One characteristic feature of the present invention is use of an adduct in dry state of a particular component (a) and hydrogen peroxide (b) in such assay.

Component (a) is at least one member selected from the group consisting of a carboxylic acid and a salt thereof, phosphoric acid and a salt thereof, and a sulfonic acid and a salt thereof; at least one member selected from the group consisting of a monosaccharide, a disaccharide, a sugar alcohol, and polymers thereof; or at least one member selected from the group consisting of a N-acetylglucosamine, ascorbic acid, creatinine, and polyethylene glycol.

The component (a) which is at least one member selected from the group consisting of a carboxylic acid and a salt thereof, phosphoric acid and a salt thereof, and a sulfonic acid and a salt thereof may be any component that has a high hydrogen peroxide-retaining ability and little influence on the activities of analyte and reagent components like protein.

Exemplary carboxylic acids include a monocarboxylic acid, a dicarboxylic acid, a tricarboxylic acid, a tetracarboxylic acid, a uronic acid, and a polyuronic acid.

Preferably, an aliphatic monocarboxylic acid of the monocarboxylic acid is the compound represented by general formula (1) or pyruvic acid. Exemplary the compounds represented by general formula (1) include acetic acid, glycolic acid, propionic acid, 3-hydroxypropionic acid, 2,2-bis(hydroxymethyl)propionic acid, lactic acid, glyceric acid, gluconic acid, glucoheptonic acid, 4-hydroxyphenylacetic acid, hydantoic acid, citrulline, albizziin, serine, alanine, threonine, N-acetylglycine and salts thereof; among which acetic acid, 3-hydroxypropionic acid, 2,2-bis (hydroxymethyl)propionic acid, lactic acid, glyceric acid, glycolic acid, glucoheptonic acid, 4-hydroxyphenylacetic acid, hydantoic acid, citrulline, albizziin, L-serine and N-acetylglycine being preferred in view of their high hydrogen peroxide-retaining ability and little degree of inhibition of the antigen-antibody reaction and enzyme reaction. Particularly preferred are acetic acid, lactic acid, hydantoic acid, N-acetylglycine and salts thereof in view of their high solubility in water and speediness of the assay.

Further, exemplary aromatic monocarboxlic acids include vanillic acid, picolinic acid and the like; among which vanillic acid and the salts thereof are preferably used in view of their high hydrogen peroxide-retaining ability and little degree of inhibitor of the antigen-antibody reaction and enzyme reaction.

Exemplary dicarboxylic acids include aliphatic dicarboxylic acids and aromatic dicarboxylic acids such as oxalic acid, malonic acid, methylmalonic acid, succinic acid, oxaloacetic acid, methylsuccinic acid, 2,2-dimethysuccinic acid, maleic acid, fumalic acid, citraconic acid, acetylene-dicarboxylic acid, malic acid, citramalic acid, tartaric acid, glutaric acid, diglycolic acid, 2-ketoglutaric acid, 3-ketoglutaric acid, 3-methylglutaric acid, 3-hydroxy-3- methylglutaric acid, adipic acid, mucic acid, pimelic acid, suberic acid, 1,2-cyclohexanedicarboxylic acid, 1,4-cyclohexanedicarboxylic acid, glutamic acid, N-(2-acetamid)iminodiacetic acid, o-phthalic acid, isophthalic acid, terephthalic acid, 4-hydroxyphthalic acid, 4-hydroxyisophthalic acid, 5-hydroxyisophthalic acid. Among which the preferred are oxalic acid, malonic acid, methylmalonic acid, succinic acid, methylsuccinic acid, maleic acid, malic acid, citramalic acid, tartaric acid, glutaric acid, diglycolic acid, 3-hydroxy-3-methylglutaric acid, mucic acid, pimelic acid, 1,2-cyclohexanedicarboxylic acid, 1,4-cyclohexanedicarboxylic acid, glutamic acid, N-(2-acetamid) iminodiacetic acid, o-phthalic acid, isophthalic acid, 4-hydroxyphthalic acid, and 4-hydroxyisophthalic acid, and the most preferred are malonic acid, L-(+)-tartaric acid, DL-tartaric acid, pimelic acid, isophthalic acid and 4-hydroxyisophthalic acid. The acids and the salts thereof are preferred in view of their high hydrogen peroxide-retaining ability and little degree of inhibition of the antigen-antibody reaction and enzyme reaction, and in view of their high solubility in water and speediness of the assay.

Exemplary tricarboxylic acids which are preferable for use in the present invention include the compounds represented by general formulae (2) and (3) such as citric acid, aconit acid, and 1,3,5-pentatricarboxylic acid. Among these, the preferred is citric acid and the salts thereof in view of their high hydrogen peroxide-retaining ability and little degree of inhibition of the antigen-antibody reaction and enzyme reaction, and in view of its high solubility and speediness of the measurement.

Exemplary preferable tetracarboxylic acids are the compounds represented by general formula (4). Among such compounds, the preferred is butane-1,2,3,4-tetracarboxylic acid since the acid and the salts thereof are preferred in the view of their high hydrogen peroxide-retaining ability and little degree of inhibition of the antigen-antibody reaction and enzyme reaction, and in view of their high solubility in water and speediness of the assay.

Use of a uronic acid, a polyuronic acid, or a salt thereof is preferable as the component (a) of the present invention because they may serve a hydrogen peroxide-retaining sol or gel, or impart the hydrogen peroxide-retaining matrix with a hydrogen peroxide-retaining ability. Preferable uronic acids include glucuronic acid, guluronic acid, mannuronic acid, galacturonic acid, and iduronic acid. Among these, the most preferred is glucuronic acid in view of their high hydrogen peroxide-retaining ability and little degree of inhibition of the antigen-antibody reaction and enzyme reaction, and in view of their high solubility in water and speediness of the assay.

The polyuronic acids used may be a homopolymer of the above-mentioned uronic acid or a heteropolymer of the above-mentioned uronic acid. The heteropolymer may include one with aldose. Exemplary polyuronic acids are arginic acid and pectic acid, the most preferred being arginic acid.

Preferable sulfonic acids are a hydroxyalkanesulfonic acid, aminoalkanesulfonic acid, hydroxybenzenesulfonic acid. Exemplary preferred are isethionic acid, taurine, cysteic acid, and guaiacol sulfonic acid. Cysteic acid and the salt thereof are most preferable. Use of a hydroxyalkanesulfonic acid or a salt thereof for the component (a) of the present invention is particularly preferable when the presence of carboxyl group or phosphono group is unfavorable for the assay in view of chelate effect or the like.

Exemplary compounds having both sulfo group and carboxyl group include cysteic acid and chondroitin sulfate, and use of such compounds are also preferable.

Preferable salts of carboxylic acids, phosphoric acid, and sulfonic acids which may be used for the component (a) include an alkaline metal salt and an alkaline earth metal salt of the carboxylic acids, phosphoric acid, or sulfonic acid. The most preferred are sodium salt and potassium salt of the above-mentioned acids.

The monosaccharides which may be used in the present invention include a pentose, a hexose, and a heptose. Among these, preferable hexoses are glucose and galactose. The disaccharides preferable for use are saccharose, maltose, lactose, and trehalose. Preferable sugar alcohol is mannitol. Preferable polymers thereof are dextrane and cellulose.

The component (a) may be used at a concentration adequately selected in accordance with the hydrogen peroxide-retaining ability of the component. The component (a), however, is preferably used at a concentration of from 0.01 to 1000 folds, and more preferably, from 0.1 to 100 folds in mole of the hydrogen peroxide (b). Peroxide (b) is preferably used at a concentration in aqueous solution of from 1 to 1000 mM when the hydrogen peroxide adduct is arranged in the MEDIA device, which will be described later.

In a typical production process of the adduct in dry state, the component (a) and the component (b) are mixed in an aqueous solution or in a buffer to prepare a mixed solution of the components (a) and (b), and the solvent is then removed by such means as heating, pressure reduction, or lyophilization, among which the solvent removal by lyophilization being preferable in view of the uniform adduct concentration in the resulting dried product.

When a porous matrix through which an aqueous solution is to be permeated is employed in the assay device, the porous matrix may be directly impregnated with the above-described mixed solution and dried.

Alternatively, a functional group such as carboxyl group, phosphono group, sulfo group, or the like may be preliminarily introduced in the porous matrix such as a filter paper made of a natural fiber (cellulose), a synthetic resin, a synthetic fiber, or the like to thereby impart the matrix which is to be impregnated with the hydrogen peroxide with the hydrogen peroxide-retaining ability. The thus treated porous matrix may be directly impregnated with aqueous solution of hydrogen peroxide, and dried to prepare the hydrogen peroxide-retaining matrix. All of these are suitable for use as carboxyl group, phosphono group, sulfo group, or salts thereof of solid substances.

Alternatively, water-soluble high polymers such as polyuronic acid, polyacrylic acid, and carboxymethyl cellulose (CMC) may be used for the hydrogen peroxide-retaining support, gel, or sol. A mixture of such hydrogen peroxide-retaining support, gel, or sol with hydantoic acid, L-citrulline, citric acid, or phosphoric acid may be used for the hydrogen peroxide-retaining reagent. The uronic acids which may be used include glucuronic acid, guluronic acid, mannuronic acid, galacturonic acid, and iduronic acid. The polyuronic acids which may be used are a homopolymer of the above-mentioned uronic acid or a heteropolymer of the above-mentioned uronic acid. Such heteropolymer includes a heteropolymer of the said uronic acid with aldose. Exemplary such polyuronic acids are arginic acid and pectic acid.

In the assay of the present invention, an aqueous solution is added to the adduct of components (a) and (b) to thereby generate peroxide solution, illustratively hydrogen peroxide solution, which is used for a reagent in the assay. An aqueous solution is a solution containing water as its main component, into which peroxide is to dissolve to constitute the aqueous solution of peroxide. Typical such aqueous solution include water, a saline, a buffer, and a liquid sample, and typical liquid samples are urine, serum, plasma, whole blood, saliva, tear, spinal fluid, and nipple discharge. A mucous fluid, body tissue, cells or bacteria in the form of a solid, gel or sol suspended or dissolved in a liquid such as a buffer, an extraction solution or a solvent may also be used for the liquid sample.

The aqueous solution may be added to the adduct by direct mixing of the aqueous solution and the adduct. However, when the above-described porous matrix is used in the assay device, the porous matrix having the dried adduct attached thereto may be impregnated with the aqueous solution. When the aqueous solution is brought in contact with the adduct, peroxide, typically hydrogen peroxide dissolves out of the matrix to use the assay device. In the assay method of the present invention, component (a) does not denature the proteins involved in the assay, or inhibit the immunoreaction (a specific reaction of the analyte) or the enzymatic reaction (the reaction of the labeling agent). Component (a), therefore, may be located at the site of the reaction in advance, or alternatively, in the upstream of the reaction site so that the components (a) and (b) which dissolved in the aqueous solution would be transported to the reaction site. The components (a) and (b) can be located in the downstream of the reaction site so that the both components would be permeated to the reaction site. When the adduct is located near the reaction site, hydrogen peroxide, which is an assay reagent, is brought into an active state in a shorter period of time. In the specific reaction of the analyte, little inhibitory effect of the component (a) is recognized since the component (a) has little adverse effects, and the adduct with a high hydrogen peroxide-retaining ability may realize the use of the component (a) at a low concentration.

Next, embodiments utilizing the assay of the present invention is described.

For example, in the tests of occult blood, a sample such as urea, feces, or feces extract is brought in contact with hydrogen peroxide in the presence of a chromogenic agent such as o-triazine, guaiacol, tetramethylbenzidine, or the like to thereby detect peroxidase activity of hemoglobin in the sample by the color development of the chromogenic agent. In conventional assay kit, hydrogen peroxide is bundled with the kit in the state of a solution so that it may be added dropwise to the sample collection device such as filter paper or stick having the sample attached thereto, or into the sample collection container having the sample accommodated therein. In the case of the present invention, hydrogen peroxide in the form of a dried adduct may be preliminarily located on the sample collection device or in the sample collection container such as a filter paper or stick having the sample attached thereto since the hydrogen peroxide adduct is stable in dry state and does not adversely effect the enzymatic reaction process as in the case of urea. For example, a filter paper having a chromogenic agent impregnated therein may be overlayed with a filter paper having the hydrogen peroxide adduct of the present invention impregnated therein, and the former and the latter may be located adjacent to each other on sample collection device or in the sample collection container. In such occult blood test, color development reaction may be induced immediately after the sample collection. Even when the sample collected is a solid such as feces, and dropwise addition of a moisture to the solid sample is required, a buffer, and not the unstable hydrogen peroxide, can be bundled with the test kit. As described above, even in occult blood test, use of the hydrogen peroxide adduct of the present invention results in an improved stability of the assay reagents and convenience of the assay procedure.

In the case of the chemiluminescence assay as mentioned above, the chemiluminescence should be detected simultaneously with dispensation of the trigger solution containing hydrogen peroxide or the reagent which triggers the following luminescence reactions. Therefore, a precise interlock between the trigger solution-dispensing/stirring mechanism and the chemiluminescence detection mechanism is required. However, if the hydrogen peroxide adduct in dry state of the present invention is preliminarily incorporated in the reaction container, hydrogen peroxide may be generated to thereby induce the chemiluminescence by merely dispensing the sample solution into the reaction container. Another preferable assay process is use of a fine particle support such as a magnetic particle for the immobilization of the specific binding substance. In this case, the fine particle support which has undergone the specific binding reaction may be captured by a filter such as a filter paper, and the component required for chemiluminescence may be added dropwise onto the filter so that the chemiluminescence generated by the label trapped on the fine particle support may be observed on the filter. The hydrogen peroxide adduct of the present invention can be stably impregnated and dried in the filter such as a filter paper, and therefore, if the fine particle support that has undergone the specific binding reaction is captured by using the dried filter having impregnated therewith the hydrogen peroxide adduct of the present invention, chemiluminescence can be induced with no dropwise addition of the hydrogen peroxide to thereby enable a quick, accurate chemiluminescence specific binding assay.

As will be appreciated by reading the foregoing description, the assay of the present invention may be utilized in all assays wherein peroxide is used as an assay reagent including the assay procedures as described above to improve the stability of the assay reagents and convenience of the assay operation, and to enable an accurate, quick assay.

The assay of the present invention is particularly preferable for use in the assays utilizing peroxidase activity such as occult blood test, the assays utilizing chemiluminescence, and the assays utilizing specific a binding reaction comprising the specific binding assay using the assay device provided with a flow path and a detection means.

Next, the assay of the present invention is described in detail by referring to an embodiment of the assay device utilizing the assay of the present invention.

The principle of the assay device for conducting the assay of the present invention is not limited to any particular type so long as peroxide is utilized in the assay. The assay of the present invention, however, is particularly suited for use in the specific binding assay known as MEDIA (mediator diffusion-controlled immunoassay) as disclosed in Japanese Patent Application Laid-Open No. 5(1993)-264552 (EP 0 525 723 A2) and Japanese Patent Application Laid-Open No. 7 (1995)-234201 wherein HRPO (an oxidoreductase whose substrate is hydrogen peroxide, and which is used for the labeling agent) is developed through the matrix with the liquid sample to form a distribution of the labeling agent (a distribution of the labeling agent at various distance from the electrode) by the specific binding reaction between the analyte in the liquid sample and the specific binding substance, and the current intensity corresponding to the analyte concentration of the liquid sample which is controlled by diffusion of the electron mediator is measured to thereby determine the concentration of the analyte.

In view of such situation, the basic principle of the MEDIA-type specific binding assay wherein the present invention may be incorporated is described by referring to an embodiment wherein the assay of the present invention is practiced in an assay device adapted for MEDIA-type specific binding assay. It should be noted that the terms used herein are those defined in Japanese Patent Application Laid-Open Nos. 5(1993)-264552 and 7(1995)234201, which are herein incorporated by reference.

An embodiment of the assay device which may be used for the assay of the present invention is provided with a flow path e and a detection means c. The principle of the assay device is schematically shown in FIG. 1, and the exploded view of such assay device is shown in FIG. 2.

The flow path e is the pathway of the liquid sample that has been introduced into the assay device from a sample-introducing means a. The flow path e is the field wherein the analyte and the signal substance generator are developed and wherein the specific binding reaction takes place.

The liquid sample introduced from the sample-introducing means a is guided to the flow path e by means of an external force such as pressure applied by a pump or gravity and/or spontaneous penetration.

In order to reproducibly guide the liquid sample into the flow path e by a simple structure, the flow path e is preferably constituted either from a capillary tube/narrow gap or a porous member to allow the spontaneous penetration of the liquid sample into the flow path e.

In an embodiment of the flow path e, the specific binding substance is attached to the capillary tube or the porous member constituting the flow path e, and when the liquid sample and the signal substance generator flows through the flow path e in a predetermined direction, the specific binding reaction occurs with a particular distribution of the signal substance generator in the flow direction within the flow path e. In an exemplary assay process, the specific binding reaction occurs at various positions within the flow path e to form a particular distribution in the flow direction, namely, a particular distribution of the signal substance generator in the flow direction in correspondence with the concentration of the analyte in the liquid sample by a competitive specific binding reaction of the analyte and the signal substance generator to the specific binding substance; or a specific binding reaction of the analyte to the specific binding substance followed by a sandwich-type specific binding reaction of the signal substance generator to the analyte.

The flow path e wherein the specific binding reaction or the like occurs to form a particular distribution of the signal substance generator in the flow direction is not limited to the embodiments wherein the specific binding substance is immobilized within the flow path e, and in alternative embodiments, the flow path e may be so constituted that changes in molecular weight or particle size caused by the specific binding reaction may be reflected in the final distribution of the signal substance generator.

A detection means c is the site where a signal is produced upon arrival of the signal substance threreto and where the thus produced signal is detected. The signal produced may be monitored either by visual inspection with naked eye or by an appropriate additional apparatus suitably selected in accordance with the characteristics of the signal as a change in signal intensity.

The specific binding substance, the signal substance generator, and the substance involved in the generation of the signal as described above may be incorporated in the assay device either at the time of the production of the assay device, or at the time of the use of the assay device before or simultaneously with or after the introduction of the liquid sample.

When specific binding substance, the signal substance generator, and the substance involved in the generation of the signal as described above are preliminarily incorporated in the assay device, these substances may be arranged either at a uniform distribution within the device, or at a particular location within the device to be dissolved by the liquid sample and/or other development liquid.

In the assay device as described above, the hydrogen peroxide adduct, which is the critical feature of the present invention, serves the substance involved in the generation of the signal substance. Since the hydrogen peroxide adduct has little adverse effect on the specific binding reaction, the hydrogen peroxide adduct can be located in the upstream portion of the flow path e to realize the arrival of the aqueous solution of hydrogen peroxide to the field of the specific binding reaction immediately after the dissolution of the hydrogen peroxide adduct. Results of the assay is thereby obtained in a short while.

If desired, an absorption means may be provided in the direct downstream of the flow path e to enhance the spontaneous flow of the liquid sample or to increase the volume of the liquid sample passing through the flow path e.

The absorption means may be constituted from a water absorption material, and if desired, the substance involved in the generation of the signal substance and the like may be retained in this absorption means. The introduced sample solution is sucked by and retained in this absorption means.

As mentioned above, the principle of the assay device which may be used for the assay of the present invention is schematically shown in FIG. 1. The assay device comprises the sample-introducing means a from which the liquid sample is introduced into the assay device; a reagent portion b provided with the hydrogen peroxide adduct, and if desired, the substance involved in the generation of the signal (e.g. HRPO); the detection means c; and the matrix d directly connected to the detection means c. The sample-introducing means a, the reagent portion b, and the matrix d constitute a part of the flow path e, or the sample-introducing means a, the reagent portion b, and the matrix d are mutually connected by the flow path e. The assay device may also include a plurality of the reagent portion b.

In the embodiment of the assay device shown in FIG. 1, a liquid sample containing an unknown amount of the analyte is introduced into the assay device from the sample-introducing means a, and the thus introduced liquid sample dissolves hydrogen peroxide and the like in the reagent portion b. At least one specific binding reaction between the analyte and the specific binding substance is induced in the matrix d to form a particular distribution of the signal substance generator 10 corresponding to the amount of the analyte in the liquid sample. The signal substance 12 is then generated from the signal substance generator 10 distributed in the matrix d, in some cases, through the reaction of the signal substance generator 10 with the substance 14 involved in the generation of the signal substance. The thus generated signal substance 12 diffuses through the flow path e, and the signal produced by the signal substance 12 that arrived at the detection means c is measured in the detection means c.

FIG. 1 is a schematic view, and there is only shown one signal substance generator 10. In the actual assay system, a distribution of numerous signal substance generators 10 is formed in the matrix d, and numerous signal substances 12 are continuously generated from the thus distributed signal substance generators 10. The signals detected in the detection means c are those generated upon the arrival of the thus generated signal substances 12, and such arrival of the signal substances 12 is controlled by the diffusion of the signal substances 12, that is, the distances x of the diffusion through the matrix d from the sites where they were generated (signal substance generators 10) to the detection means c.

As will be precisely described in the following part of the specification, distribution of the signal substance generator 10 depends on the content of the analyte in the liquid sample. Therefore, when the content of the analyte in the liquid sample introduced from the sample-introducing means a is different, distribution of the distance of signal substance 12 from the signal substance generator 10 to the detection means c in the matrix d would be different in accordance with the amount of the analyte, and such difference in the distribution profile of the signal substance generator 10 is detected as a difference in the profile of the signal produced by the signal substance 12 which arrives at the detection means c.

The specific binding assay illustratively described herein is based on the principle as described above, and the amount of the analyte in the liquid sample is determined in the detection means c from the signal produced by the signal substance 12 that arrived at the detection means c.

As described above, the term "specific binding reaction" includes the reaction between the analyte and the substance which specifically binds to such analyte (including the signal substance generator 10), as well as the reaction between the specific binding substance and the signal substance generator 10.

In summary, the assay device illustratively described herein is based on the following basic concepts.

(1) When the signal substance 12 which is generated by the label of the signal substance generator 10 and which may produces a signal detectable only in the detection means c is used as a mediator, intensity of the signal observed in the detection means c reflects the distribution profile of the distance between the label (the signal substance generator 10) and the detection means c, namely, the distribution profile of the diffusion distance of the signal substance 12.

(2) Distribution of the signal substance generator 10 (namely, the label) in different profiles are formed through at least one specific binding reaction between the analyte and the specific binding substance depending on the concentration of the analyte in the liquid sample.

(3) As a result of (1) and (2), intensity of the signal observed in the detection means c reflects the concentration of the analyte in the liquid sample.

The inventors of the present invention have found the above described basic concepts, and filed a series of patent applications directed to specific binding assays and devices therefor. (See Japanese Patent Application Laid-Open No. 5(1993)-264552, EP 0 525 723 A2, and Japanese Patent Application Laid-Open No. 7(1995)-234201.) The assay based on such concept is designated as MEDIA (mediator diffusion-controlled immunoassay). When such MEDIA is conducted on an appropriate device, the analyte in the sample can be quickly assayed at a high sensitivity without conducing the troublesome removal of the reactants that failed to undergo the bond.

As described above, in the MEDIA (mediator diffusion-controlled immunoassay) described in Japanese Patent Application Laid-Open No. 7(1995)-234201, a treated glass fiber filter paper or a cellulose filter paper prepared by impregnating and drying a mixed solution of urea and hydrogen peroxide had been used for the source of the hydrogen peroxide in view of storage stability and operation convenience that preparation of aqueous solution of hydrogen peroxide would be unnecessary. It should be noted that urea had been used in view of its considerable hydrogen peroxide-retaining ability and solubility. Urea, however, is a compound which has been known as a protein denaturing agent, and presence of urea in an antigen-antibody reaction system is associated with the risk of release of the antigen that was once bound to the enzyme-labeled antibody or the immobilized antibody to result in a reduced assay reliability. In order to avoid such risk associated with the use of urea, the hydrogen peroxide adduct with urea had to be located at the downstream end of the assay device, namely, in the absorption means 28 in the case of the device shown in FIG. 2. Because of such location of the urea, the hydrogen peroxide retained by the urea was also located at a position remote from the reaction field. Since the hydrogen peroxide was supplied to the reaction system by the diffusion of the hydrogen peroxide from the downstream side, a considerable period was necessary for the establishment of a stable reaction, and to obtain the assay result. Even though the hydrogen peroxide adduct with urea was located in the downstream side of the assay device, the assay device suffered from undesirable diffusion of the urea from the downstream side that inhibited the assay reaction. In addition, the hydrogen peroxide-retaining ability of urea was not necessarily high In order to obviate such insufficiency of the MEDIA, the inventors of the present invention made an intensive study, and found that use for the peroxide source of an adduct in dry state of hydrogen peroxide with at least one member selected from a carboxylic acid and a salt thereof, a sulfonic acid and a salt thereof, phosphoric acid and a salt thereof, at least one member selected from the group consisting of a monosaccharide, a disaccharide, a sugar alcohol, and polymers thereof, and at least one member selected from the group consisting of a N-acetylglucosamine, ascorbic acid, creatinine and polyethylene glycol results in an improved hydrogen peroxide-retaining ability as well as a reduced adverse effects on the specific binding reaction and the like. The present invention has been completed on such a finding.

Next, exemplary immunoreactions (specific binding reactions) which may proceed in the matrix d are described for the cases whereinfor the cases wherein one reactant of the immunoreaction system is the analyte. In the immunoreactions illustratively described in the following, distribution of the signal substance generator 10 in the matrix d changes in accordance with the amount of the analyte in the liquid sample through the specific binding reaction. The changes of distribution are measured at detection means c.

It should be noted that various means may be adopted to change the distribution of the signal substance generator 10 in the flow path in accordance with the amount of the analyte in the liquid sample. The following assays are described only by way of examples.

First type of such assays is competitive assay wherein the assay is conducted after immobilizing a substance which is the same as or analogous to the analyte in the reaction field.

In such a case, the substance which is the same as or analogous to the analyte is immobilized in the matrix d, and a complex of an anti-analyte antibody (specific binding substance) and the labeling agent (for example, the enzyme involved in the reaction that generates the signal substance 12) is used for the signal substance generator 10.

By preliminarily mixing the signal substance generator 10 with the liquid sample, and introducing the mixture into the sample-introducing means a, or by allowing the liquid sample to be mixed with the signal substance generator 10 in the reagent portion b where the signal substance generator 10 had been attached and allowing the mixed solution to flow down to the matrix d, the analyte in the sample and the immobilized substance which is the same as or analogous to the analyte are competitively reacted with the antibody (specific binding substance) moiety of the signal substance generator 10. The resulting distribution of the signal substance generator 10 will be deviated to the downstream side in the matrix d when the liquid sample contains a larger amount of the analyte.

This type of assay can be preferably used irrespective of whether the analyte is a low molecular weight substance like hapten or a high molecular weight substance. When the analyte is a hapten, the hapten which is the same as the analyte or another hapten that would undergo a cross-reaction with the specific binding substance may be immobilized in the matrix d in a manner that allows the binding of the specific binding substance to the immobilized hapten. When the analyte is a high molecular weight substance such as a high molecular weight protein, the protein itself or the peptide sequence of the epitope to which the specific binding substance binds to may be immobilized in the matrix d.

Second type of the assays is sandwich assay which is suitable for use when the analyte is a high molecular weight compound such as an antigen capable of simultaneously binding to a plurality of antibodies.

In this case, an antibody against epitope A which is the first specific binding substance against the analyte is immobilized in the matrix d, and the complex of a labeling agent and an antibody against epitope B which is the second specific binding substance against the analyte is used for the signal substance generator 10.

By preliminarily mixing the signal substance generator 10 with the liquid sample, and introducing the mixture into the sample-introducing means a, or by allowing the liquid sample to be mixed with the signal substance generator 10 in the reagent portion b where the signal substance generator 10 had been attached and allowing the mixed solution to flow down to the matrix d, the analyte in the sample is allowed to undergo a sandwich reaction. The resulting distribution of the signal substance generator 10 will be deviated to the upstream side in the matrix d when the liquid sample contains a larger amount of the analyte.

When the analyte is an antibody, an antigen which is the specific binding substance may be immobilized in the matrix d, and the complex of a labeling agent and an anti (antibody) antibody may be used for the signal substance generator 10. The analyte is then allowed to undergo the sandwich reaction.

Third type of the assays is the competitive assay wherein the specific binding substance against the analyte is immobilized in the matrix d.

In this case, an anti-analyte antibody (specific binding substance) is immobilized in the matrix d, and a complex of a substance which is the same as or analogous to the analyte (a substance which competes with the analyte for the binding to the immobilized specific binding substance) and a labeling agent is used for the signal substance generator 10. By preliminarily mixing the signal substance generator 10 with the liquid sample, and introducing the mixture into the matrix d, or by allowing the liquid sample to be mixed with the signal substance generator 10 in the reagent portion b in the upstream of the matrix d and allowing the mixed solution to flow down to the matrix d, the analyte in the sample and the signal substance generator 10 are competitively reacted with the immobilized specific binding substance. The resulting distribution of the signal substance generator 10 will be deviated to the downstream side in the matrix d if the liquid sample contains a larger amount of the analyte.

If the analyte is an antibody, an antigen or an epitope thereof which is the specific binding substance of the analyte may be immobilized in the flow path, and a complex of another antibody which competes with the analyte antibody for the binding to the immobilized specific binding substance and the labeling agent may be used for the signal substance generator 10.

In the above-described assays, an antibody or an antigen is immobilized in the matrix d, and the signal substance generator 10 and the analyte are directly or indirectly bound to the antibody. Change in the distribution of the signal substance generator 10 in accordance with the amount of the analyte may be induced even if the signal substance generator 10 and the analyte are not bound to the matrix d, namely, if the antibody or the antigen in the above-described exemplary assays is not immobilized in the matrix d. Such assays are also within the scope of the present invention.

For example, when the analyte is a microorganism (e.g. a pathologic fungus), and the signal substance generator 10 is a labeled specific binding substance comprising a complex of an anti-microorganism antibody (e.g. an anti-pathologic fungus antibody) and a labeling agent, a large difference in the development speed through the matrix d, namely, in the final location in the matrix d is generated between the complex of the analyte and the signal substance generator 10 and the free signal substance generator 10 since the analyte (the microorganism) is considerably larger than the signal substance generator 10.

In such a case, a clear difference in the final location may be produced, for example, by constituting the matrix d from a porous material having an adequately selected mesh (pore size), or by using a gel or sol matrix having a viscosity adequately selected in accordance with the size of the microorganism.

In this case, the analyte (the microorganism) could be localized in the matrix d although it not bound to the matrix d, and the signal substance generator 10 which could undergo a specific binding reaction with the analyte will be distributed in a profile corresponding to the amount of the analyte in the matrix d.

The assay of the present invention using the adduct of the component (a) and the hydrogen peroxide (b) for the assay reagent is also applicable in such a case.

Another exemplary assay is the assay utilizing spontaneous formation of precipitatory complex (immunoprecipitate) between the free labeled antibody and the free analyte (so called gel immunoprecipitation).

In such a case, the amount of the immunoprecipitate formed varies in accordance with the amount of the analyte. The immunoprecipitate formed is retained in the upstream side of the matrix d comprising the porous material and/or the gel, while the free labeled antibody which was not involved in the immunoprecipitation reaction is developed to the downstream side of the matrix d. The distribution of the signal substance generator 10 thus varies in accordance with the amount of the analyte in the sample.

In a similar manner, change in the size of the associated fine particles by a specific binding agglutination reaction between a fine particle support having the specific binding substance immobilized thereto and the analyte may also be utilized to change the distribution profile of the signal substance generator 10.

The assay of the present invention using the adduct of the component (a) and the hydrogen peroxide (b) for the assay reagent is also applicable in such a case.

Next, generation of the signal in the specific binding reaction is described by referring to FIG. 1 for the case wherein the signal substance generator 10 is a peroxidase-labeled specific binding substance.

The hydrogen peroxide (the substrate for an enzyme) supplied from the hydrogen peroxide adduct is reduced into water by peroxidase (a component of the labeled specific binding substance), and at the same time, an electron mediator (hydrogen donor) is oxidized into an oxidized electron mediator. The thus formed oxidized electron mediator induces an oxidation-reduction reaction (an electrochemical reaction) at the electrode (detection means c) to produce an electric signal.

In the present invention, the term, electron mediator is used to generally designate oxidation-reduction compounds which mediate the enzymatic reaction and the electrode reaction to realize electron transfer between both reactions. The electron mediators include those which do not substantially generate any irreversible byproduct in either reaction, and which may be cycled between both reactions.

In FIG. 1, when the substances involved in the generation of the signal substance (hydrogen peroxide and the reduced electron mediator) 14 react with the signal substance generator (peroxidase-labeled specific binding substance) 10 in the matrix d, the reduced electron mediator is converted into the oxidized electron mediator, which is the signal substance 12. When this signal substance 12 diffuses to reach the detection means c (electrode) by diffusion adjusted to a potential of −150 mV (vs Ag/AgCl), the signal substance is reduced back to the reduced electron mediator simultaneously with the generation of the signal in terms of reduction current (electron transfer).

Exemplary reduced electron mediators which may serve the substance involved in the generation of the signal substance 14 include hydroquinone, p-phenylenediamine (PPD), N,N-dimethyl-p-phenylenediamine (DMPD), N,N,N',N'-tetramethyl-p-phenylenediamine (TMPD), N,N,N',N'-tetraethyl-p-phenylenediamine (TEPD), N,N,N',N'-tetrakiscarboxymethyl-p-phenylenediamine (TCPD), N,N,N',N'-tetrakis(2-hydroxyethyl)-p-phenylenediamine (THEPD), N,N,N',N'-tetrakis(2,3-dihydroxypropyl)-p-phenylenediamine (TDHPD), and the like. The preferred are TDHPD, TCPD, and THEPD.

The flow path e may comprise a porous matrix, a gel matrix, or the like. When a gel matrix is used for the flow path e, use of a matrix which is converted to gel or sol state upon contact with the sample liquid is preferred. Preferably, the flow path e comprises a porous matrix, or a porous matrix having a water-soluble high molecular weight compound impregnated therein in dry state. The flow path e may also comprise a porous matrix having a solid substance loaded thereto.

Exemplary porous matrices which may be used for the flow path e include porous membranes made from cellulose, cellulose acetate, nitrocellulose, or nylon; filter papers made from glass fiber or cellulose fiber; porous ceramic; and the like. Exemplary gel matrices include agar, agarose, dextran, and polyacrylamide. Exemplary water-soluble high molecular weight compounds which may be impregnated in the porous matrix include starch and derivatives thereof, mannan, galactan, agar, agarose, sodium arginate, gum Arabic, dextran, gelatin, casein, collagen, methylcellulose (MC), ethylcellulose (EC), hydroxyethylcellulose (HEC), carboxymethyl cellulose (CMC), polyvinyl alcohol (Poval), sodium polyacrylate, and the like. Exemplary solid substances which may be retained on the porous matrix include fine particles such as porous particle of dextran, latex such as polystyrene latex, and fine glass particles, and those imparted with active groups for the binding purpose.

By constituting the flow path e in various structures from various materials, for example, in the form of a laminate, properties of the flow path e may be varied freely.

For example, when a material with a smaller pore size is used for the flow path e near the detection means c, and a material with a larger pore size is used for the flow path e near the sample introduction means a, a clearer difference in the distribution profile of the signal substance generator corresponding to the difference in the amount of the analyte may be produced after the specific binding reaction. Exemplary matrices which may realize such conditions include a polyacrylamide gradient gel and a laminate of porous membranes of different pore sizes.

In immobilizing the specific binding substance for the analyte in the matrix d, the specific binding substance may be immobilized either uniformly throughout the matrix d, or locally in one part of the matrix d. Alternatively, the specific binding substance may be immobilized in a concentration gradient so that a larger proportion of the specific binding substance would be present in the upstream side and a smaller proportion of the specific binding substance would be present in the downstream side.

It should be noted that the specific binding substance may be immobilized on the matrix d either by covalent bonding or adsorption of the specific binding substance to the porous matrix or the gel matrix. When the matrix d comprises a plurality of members; the porous matrix and the water-soluble high molecular weight compound; or the porous matrix and the solid substance retained therein, the specific binding substance may be immobilized either on all of the components/members constituting the matrix d or on some of the components/members constituting the matrix d.

The amount of the sample required may be reduced by reducing the length (in flow direction of the sample) of the flow path e of the assay device of the present invention. However, if the length is excessively reduced, the change in the distribution profile of the signal substance generator in accordance with the amount of the analyte would become unclear. The length of the flow path e is generally in the range of from 10 $\mu$m to several ten mm.

The detection means c is the site where the signal produced upon arrival of the signal substance 12 is detected by visual inspection with naked eye, or in terms of change in the signal intensity by the additionally equipped measuring apparatus adequately selected in accordance with the nature of the signal. The detection means c is located at a position where it can receive the signal substance 12 from the matrix d.

Preferably, the detection means c is located at a position where a sufficient change in the signal intensity caused by the change in the distribution profile of the signal substance generator 10 may be observed. The detection means c is generally located at the downstream end or the upstream end of the matrix d.

The detection means c is not limited to any particular type, and various known means may be utilized according to the signal produced by the signal substance (or the signal produced by the detection means by the mediation of signal substance). Use of electrochemical detection means is preferable.

When an electrochemical signal is detected, electrodes of various types may be employed. Exemplary electrodes which can be used for a working electrode and a reference electrode include electrodes of platinum, gold, silver, and carbon. Use of a carbon printed electrode is preferable in view of the production convenience. In such a case, the plate of the electrode may comprise either a liquid impermeable plate such as PET film, vinyl chloride plate, or glass plate, or a liquid-permeable sheet such as filter paper. If a finer electrode constitution is required, a microelectrode or a microarray electrode may be prepared.

Exemplary counter electrodes are Ag and Ag/AgCl electrodes. Such counter electrodes may also be provided by printing or the like.

Specificity and sensitivity of the electrode reaction may be improved when an enzyme electrode is employed for the detection means c. In such a case, the signal substance functions as the substrate or cofactor of the enzyme electrode, and the signal is detected upon receipt of the electron by the electrode.

The enzyme electrode used may be selected from those used in biochemical assays or those known in the field of analytical chemistry.

When the signal is fluorescence, luminescence or color development, the detection means c may comprise a luminescence generation member having at least one substance involved in the production of the signal required in the luminescence reaction substantially immobilized thereto; a fluorescence generation member having at least one substance involved in the production of the signal required in the fluorescence reaction substantially immobilized thereto; or a color development member having at least one substance involved in the production of the signal required in the color development reaction substantially immobilized thereto.

Immobilization of such a substance may be effected, for example, by utilizing a glass board which has been treated with 3-aminopropyltriethoxysilane with glutalaldehyde. Various methods may be used for the immobilization.

In the assay device, the reagent portion b provided with the hydrogen peroxide adduct and the like is preferably arranged in the upstream of the matrix d. When an aqueous solution is brought in contact with the thus arranged hydrogen peroxide adduct, hydrogen peroxide will dissolve into the aqueous solution. The resulting aqueous solution of the hydrogen peroxide will directly flow into the flow path in the downstream of the reagent portion b to induce the signal substance-generating reaction catalyzed by peroxidase to thereby produce the electric signal in the detection means c. When the reagent portion b is arranged in the upstream of the matrix d, the assay result can be obtained faster than the assay device in which the reagent portion b is arranged in the downstream of the matrix d, wherein the hydrogen peroxide is supplied by diffusion from the downstream side.

It is noted that the hydrogen peroxide adduct of the present invention has beneficial properties such as extreme hydrogen peroxide-retaining ability, low adversely reactivities to the assay reactions, good solubility and good stability, and such benefits are useful despite of any arranging portion in any assay devices.

PREFERRED EMBODIMENTS OF THE INVENTION

Figure 4:
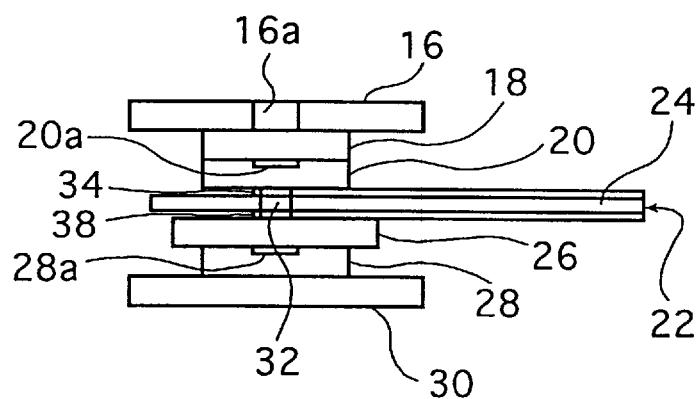
FIG. 4 is a schematic cross-sectional view of the specific binding assay (MEDIA) device of FIG. 2 after its assembly.

FIG. 2 is an exploded perspective view of a preferable embodiment of the specific binding assay device for MEDIA of the present invention wherein the assay is conducted by means of electrochemical signals. FIG. 4 is a cross-sectional view of the specific binding assay device in FIG. 2 after its assembly.

The assay device shown in FIG. 2 is constituted, from the top, a top cover 16, a first reagent-impregnated member 18, a second reagent-impregnated member 20, an electrode member 22 having one or more detection unit, a specific binding substance-immobilized flow path (matrix) 26, an absorption member 28, and a bottom board 30. As shown in FIG. 2, such members are assembled by disposing one member on another member from the bottom to the top.

In the assay device shown in FIGS. 2 and 4, a sample-introducing unit is constituted by the top cover 16 (a sample inlet port 16a provided therein), the first reagent-impregnated member 18, and the second reagent-impregnated member 20. It necessary, a filter member and other necessary members may be provided in this sample-introducing unit in addition to the first reagent-impregnated member 18, and the second reagent-impregnated member 20.

The top cover 16 is molded from a resin such as polyvinyl chloride, epoxy, acryl or PET (polyethylene terephthalate), and the sample inlet port 16a is formed in its center.

The first reagent-impregnated member 18 and the second reagent-impregnated member 20 are suitably arranged depending on the type of the sample solution, analyte, the specific binding reaction utilized in the assay, and the like. The first reagent-impregnated member 18 and the second reagent-impregnated member 20 may respectively comprise a dried matrix such as a glass fiber filter paper sheet, a cellulose filter paper sheet, or a nonwoven sheet which has been impregnated with a solution containing the reagents required for the assay such as a signal substance generator, a substance involved in the generation of a signal substance, a substance involved in the generation of a signal, and an electron mediator, a stabilizing and/or protecting agent therefor, a salt component for adjusting ion strength and/or pH, a buffer component, a surfactant, reagents for allowing a smooth flow of the sample solution such as a blood anti-coagulant and the like.

When the signal substance generator is a HRPO-labeled specific binding substance, hydrogen peroxide, which is a typical substance involved in the generation of the signal substance, may be used in the form of a hydrogen peroxide adduct, and impregnated and dried in any one of the reagent-impregnated members.

When the sample solution passes through the first reagent-impregnated member 18 and the second reagent-impregnated member 20, hydrogen peroxide dissolves out of the matrix together with the signal substance generator to be mixed with the sample solution and to be involved in the reaction.

It should be noted that the reagent-impregnated member may retain one or more substances, and that the reagent-impregnated member may not necessarily comprise two separate first and second reagent-impregnated members 18 and 20 as in the case of the embodiment shown in the drawings. It is permitted that a single reagent-impregnated member, or alternatively, three or more reagent-impregnated members are set up.

Provision of the first and second reagent-impregnated members 18 and 20 also contributes for the reduction of the flow speed of the sample solution, and a sufficient reaction period is thereby ensured.

In the preferred embodiment shown in the drawings, a water-impermeable seal member 20a is disposed in the center of the upper surface of the second reagent-impregnated member 20.

Provision of such a seal member 20a results in the change of the flow direction of the sample liquid from vertical to horizontal direction, and a longer flow period of the sample solution, and hence, a sufficient reaction period are ensured.

Such a change in the flow direction also results in the mixing of various components involved in the reaction, and hence, in an improved reaction efficiency. An accurate measurement is thereby realized. The seal member 20a may be formed by non-limited suitable procedure from a non-limited material. The seal member 20a comprising a water-impermeable material such as vinyl chloride, cellulose acetate, polyester, or the like may be adhered to the central portion of the second reagent-impregnated member 20 by such means as an acrylic adhesive. Alternatively, the seal member 20a may be provided by forming a thin film of a water-impermeable resin or polymer on the second reagent-impregnated member 20 by such means as printing, photo polymerization, or photo-curing.

The electrode member 22 is provided with one or more detection means c. In the assay device shown in the drawings, the electrode member 22 comprises an insulation board 24 of PET (polyethylene terephthalate) or the like provided, on its upper surface, with a reference/counter electrode 34, and on its lower surface, with a work electrode 38 which serves the detection means. The electric signal corresponding to the distribution of the signal generator formed in the flow path 26 may be detected at the work electrode 38.

Figure 3A:
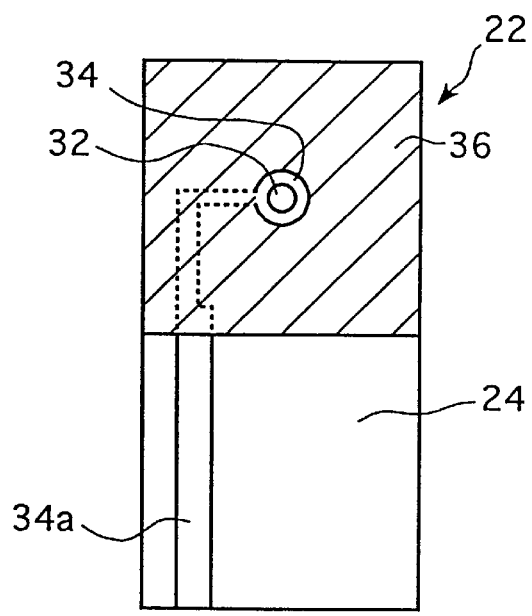
FIGS. 3(a) and 3(b) are respectively schematic views of the upper surface (FIG. 3(a)) and the lower surface (FIG. 3(b)) of the electrode member of the specific binding assay (MEDIA) device shown in FIG. 2.
Figure 3B:
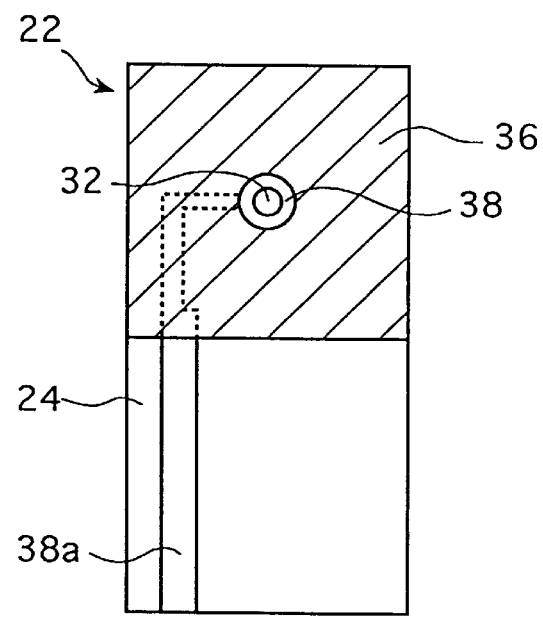

The upper surface of the electrode member 22 is shown in FIG. 3(a), and the lower surface of the electrode member 22 is shown in FIG. 3(b). On the upper surface of the electrode member 22 shown in FIG. 3(a), there are provided the counter electrode (reference electrode) 34 of annular shape and a terminal 34a thereof, and an insulation layer 36 is formed over the remaining area of the upper surface as shown by the hatching in the drawing.

On the lower surface of the electrode member 22 shown in FIG. 3(b), there are provided the work electrode 38 of annular shape and a terminal 38a therefor as in the case of the upper surface. Over the remaining area of the lower surface is also formed an insulation layer 36 as shown by the hatching in the drawing.

The insulation board 24 is formed with a through hole 32 in alignment with the counter electrode 34 and the work electrode 38.

As described above, the sample solution is guided into the flow path member 26 having a specific binding substance immobilized therein after passing through the through hole 32.

In the assay device shown in the drawings, a water-impermeable seal 28a is provided under the flow path member 26, and therefore, the sample solution that entered from the through hole 32 (and namely, through the interior of the work electrode 38) into the flow path member 26 flows in radially external directions.

The work electrode 38 that functions as the detection means may comprise a carbon electrode, a silver electrode, a gold electrode, or an electrode of other electrode materials. The counter electrode 34 comprises a silver electrode, a silver/silver chloride electrode, or the like.

The insulation board 24 may comprise any of the well known insulation materials such as PET, polyvinyl chloride, polyimide and polyester.

The insulation layer 36 may be formed from any of the well known insulating ink materials such as acrylic resin and polyester.

In the assay device shown in the drawings, the work electrode, the counter electrode (reference electrode), and the insulation layers may be provided by any one of the thick film formation techniques such as screen printing and doctor knife coating, or the thin film-formation techniques such as sputtering and CVD, which are well known in the art.

In the present invention, the configuration of the work electrode 38 is not limited to the ring-shaped one shown in the drawings, and two or more work electrodes 38 may be provided.

The flow path member 26 of FIG. 2 (corresponding to matrix d in FIG. 1) having a specific binding substance immobilized therein functions as the field of the specific binding reaction in the specific binding assay device adapted for MEDIA. For example, an antibody or an antigen that specifically binds to the analyte or the signal substance generator is insolubilized and immobilized on the matrix of the flow path member 26, and a distribution of the signal substance generator in a particular pattern is formed as a result of the specific binding reaction of the analyte and the like in the sample solution depending on the amount of the analyte in the sample solution. The distribution of the distance between the work electrode 38 and the signal substance generator formed in the specific binding substance-immobilized flow path member 26 is then detected in terms of current value by the mediation of the signal substance.

The specific binding substance-immobilized flow path member 26 is typically a porous membrane such as a membrane filter having a substance immobilized therein for the specific binding reaction such as an antibody, an antigen, a nucleic acid or the like, and such member 26 is prepared by impregnating and drying the solution of such specific binding substance in the porous membrane.

In the assay, the excessive sample solution passes through the specific binding substance-immobilized flow path member 26 to be absorbed in the absorption member 28, which is described below.

As mentioned above, the absorption member 28 absorbs the excess sample solution which have passed through the specific binding substance-immobilized flow path member 26. The absorption member 28, however, may have impregnated therewith the substance involved in the generation of the signal substance and/or the substance involved in the generation of the signal, for example, the hydrogen peroxide adduct of the present invention.

In the preferred embodiment of the assay device shown in the drawings, the water-impermeable seal member 28a is provided in the center of the upper surface of the absorption member 28.

As in the case of the seal member 20a, provision of such seal member 28a causes change in the flow direction of the sample liquid from vertical to the horizontal direction, and hence, increase in the period of stay within the flow path of the sample solution and improvement in the efficiency of the specific binding reaction. Distribution of the (labeled) signal substance generator in the flow path member 26 becomes more distinct to enable the measurement at a higher accuracy. It should be noted that the seal member 28a may be formed in a manner similar to the above-described seal member 20a.

The assay device shown in the drawings may be produced by stacking the above-described members in the order shown in FIGS. 2 and 3 from the bottom board 30 to the top cover 16, and fixedly securing the top cover 16 and the bottom board 30 to each other by such means as adhesion, screwing, or with a bolt and a nut.

As described above, the sample solution is introduced into the assay device from the sample inlet port 16a formed in the top cover 16.

The sample solution introduced from the sample inlet port 16a flows into the first reagent-impregnated member 18, and then into the second reagent-impregnated member 20. When the sample solution flows into the first and the second reagent-impregnated members 18 and 20, the signal substance generator, hydrogen peroxide, and the like that had been retained within the matrix in dry state dissolves out of the matrix to be mixed with the sample solution, and the specific binding reaction with the analyte is started.

As described above, in the embodiment shown in the drawings, the seal member 20a is provided on the upper surface of the second reagent-impregnated member 20 to change the direction of the sample flow from vertical to horizontal direction, and therefore, a sufficient time is provided for the reaction.

The sample solution that has passed through the second reagent-impregnated member 20 then flows through the through hole 32 in the electrode member 22, and then, into the flow path member 26 having the specific binding substance immobilized therein.

When the sample solution flows into the specific binding substance-immobilized flow path member 26, a distribution of the signal substance-generator in a particular pattern is formed in the specific binding substance-immobilized flow path member 26 through the specific binding reaction of the analyte in the sample solution. The signal substance is then generated by the action of the signal substance generator, and the signal substance diffuses and reaches the work electrode 38. At the work electrode 38, the distribution of the radial distance from the work electrode 38 to the locations of the signal substance generator in the specific binding substance-immobilized flow path member 26 is detected as a electrochemical signal corresponding to the reaction.

The excess sample solution passes through the specific binding substance-immobilized flow path member 26 to be absorbed in the absorption member 28.

The output (electric signal) from the work electrode 38 may be read after an appropriate time interval from the introduction of the predetermined amount of the sample solution in the sample inlet port, or continuously after the introduction of the sample solution.

The data obtained may be used to read intensity of the output (for example, current value) after a predetermined period of time, average value of the output intensity during a predetermined period, time required for the output to reach a predetermined intensity level, time required for the integrated value of the continuous output intensity (for example, quantity of electricity) to reach a predetermined value, and the like.

Next, the present invention is described in detail by referring to the Examples, which by no means limit the scope of the invention.

EXAMPLES

Examples 1–3 and Comparative Examples 1–4

In order to determine the compounds suitable for constituting the hydrogen peroxide adduct for the assay of the present invention, various compounds were tested and evaluated for their hydrogen peroxide-retaining ability and influence on the antigen-antibody reaction.

Example 1
Comparison of hydrogen peroxide-retaining ability
[1] The following 10 compounds
    acetic acid (Wako Junyaku Kogyo K.K.),
    3-hydroxypropionic acid (Tokyo Kasei Kogyo K.K.),
    isethionic acid (Wako Junyaku Kogyo K.K.),
    L-serine (Wako Junyaku Kogyo K.K.),
    L-citrulline (Wako Junyaku Kogyo K.K.), albizziin (Sigma),
    hydantoic acid (Tokyo Kasei Kogyo K.K.),
    N-acetylglycine (Tokyo Kasei Kogyo K.K.),
    phosphoric acid (Wako Junyaku Kogyo K.K.), and citric acid (Wako Junyaku Kogyo K.K.),
were tested and evaluated.

[2] Production of glass fiber filter paper treated with a surfactant (TWEEN 20)

A glass fiber filter paper (GA100, manufactured by Advantech-Toyo K.K.) was immersed in 0.2% aqueous solution of TWEEN 20 (Wako Junyaku Kogyo K.K.), and allowed to stand overnight at room temperature. The glass fiber filter paper was washed with distilled water for 10 times, and dried in an oven at 80° C. to prepare the glass fiber filter paper treated with a surfactant (TWEEN 20).

[3] Comparison of hydrogen peroxide-retaining ability between the compounds

Hydrogen peroxide (Wako Junyaku Kogyo K.K.) and each of the compounds listed in the above [1] were dissolved in distilled water to prepare a solution of 0.5M hydrogen peroxide and 0.5M compound. The solutions were adjusted to about pH 6.0 by adding aqueous HCl solution or aqueous NaOH solution.

The solutions were lyophilized by each of the following procedures (1), (2) and (3).

(1) The system using no matrix
    The solution was dispensed in 1.0 ml polystyrene test tube in 300 μl portions, and then lyophilized.

(2) The system wherein the reagent is loaded on a matrix of cellulose filter paper
    Round-shaped sheets of 12 mm diameter punched out from a chromatography filter paper (17 Chr, Whatman) were placed side by side on a bat, and 100 μl/sheet of the solution was spotted on the filter paper sheets. The sheets were then lyophilized.

(3) The system wherein the reagent is loaded on a matrix of glass fiber filter paper
    Round-shaped sheets of 12 mm diameter punched out from the surfactant (TWEEN 20)-treated glass fiber filter paper prepared in the above [2] were placed side by side on a bat, and 140 μl/sheet of the solution was spotted on the sheets. The sheets were then lyophilized.

Immediately after the lyophilization, the components of the lyophilizates were reconstituted by the procedure as described below to quantitate the concentration of the hydrogen peroxide in the reconstituted solution by PoroXOquant™ Quantitative Peroxide Assay kit (manufactured by PIERCE) to thereby calculate the recovery (%) of the hydrogen peroxide in relation to the amount of hydrogen peroxide that had been added before the lyophilization.

(1) The system using no matrix
    After drying the test tube, 300 μl distilled water was added to the test tube for dissolution.

(2) The system wherein the reagent is loaded on a matrix of cellulose filter paper, and (3) the system wherein the reagent is loaded on a matrix of glass fiber filter paper
    Each dried sheet was immersed in 3.0 ml of 0.1M phosphate/0.1M sodium chloride buffer solution, pH 6.0, and shaken at 150 rpm for 1 hour. The supernatant was collected.

Figure 5A:
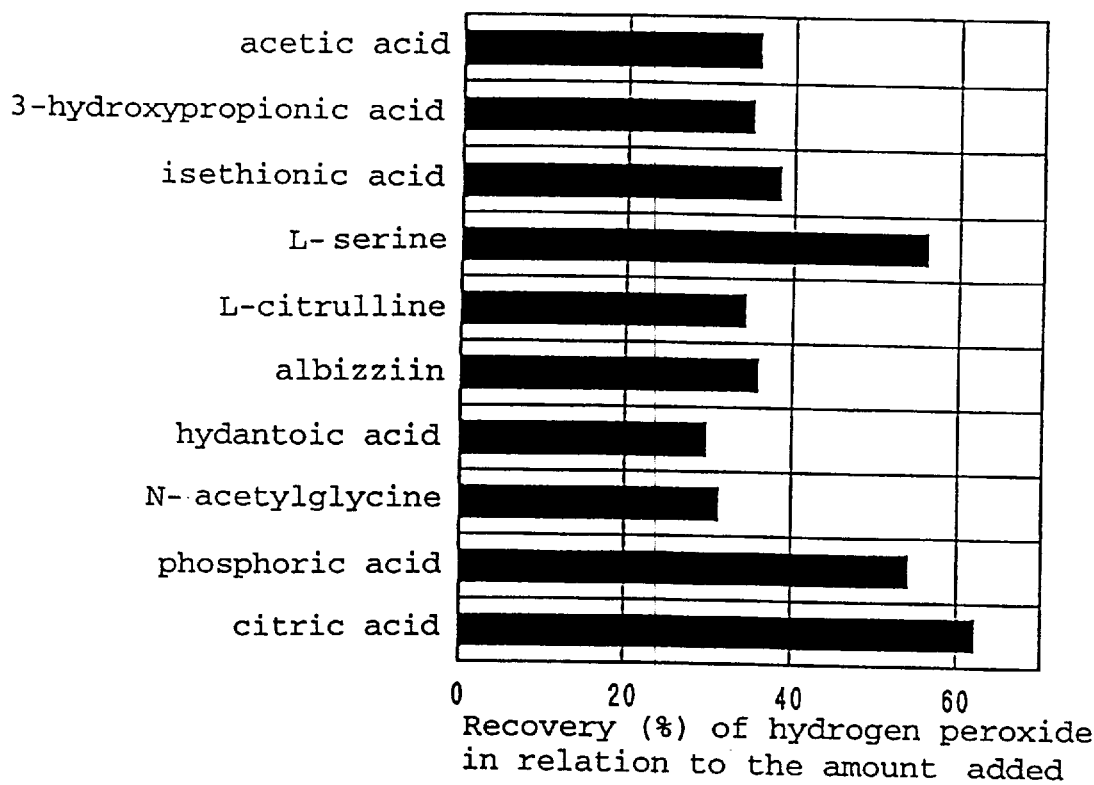
FIGS. 5(a) and 5(b) are graphs showing recovery (%) of hydrogen peroxide in relation to the amount of the hydrogen peroxide added for the cases when aqueous solution of hydrogen peroxide and various compounds of Examples of the present invention (FIG. 5(a)) and Comparative Examples (FIG. 5(b)) are lyophilized without using any matrix.
Figure 6A:
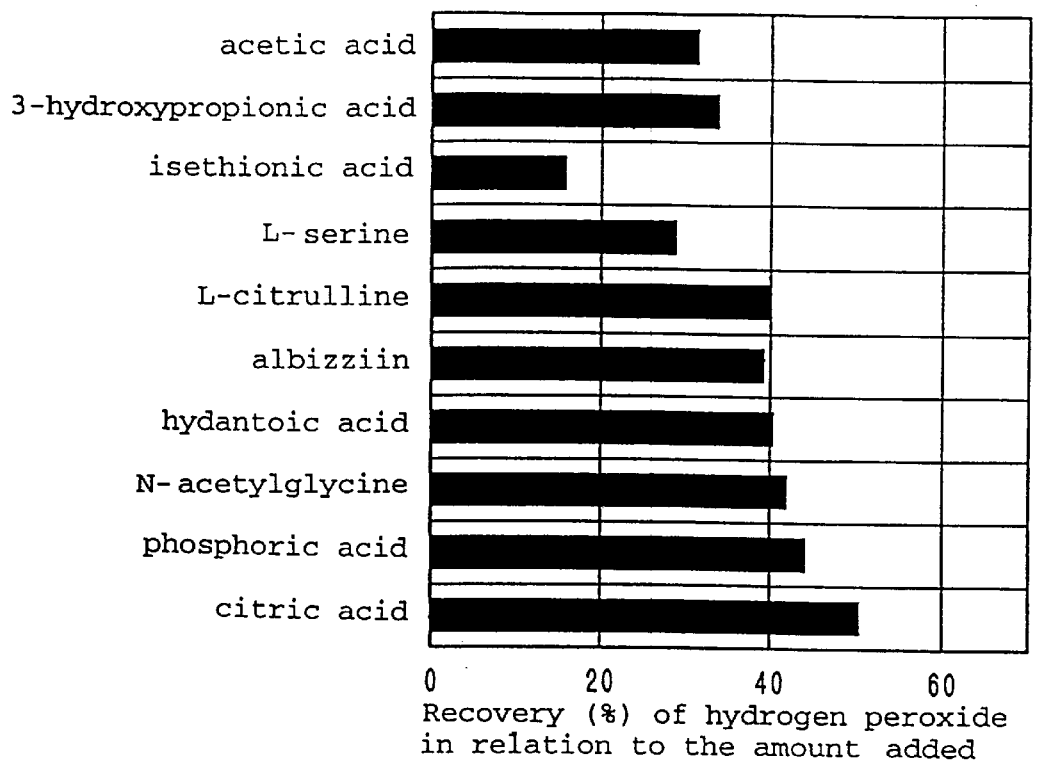
FIGS. 6(a) and 6(b) are graphs showing recovery (%) of hydrogen peroxide in relation to the amount of the hydrogen peroxide added for the cases when aqueous solution of hydrogen peroxide and various compounds of Examples of the present invention (FIG. 6(a)) and Comparative Examples (FIG. 6(b)) are impregnated in cellulose filter paper sheets and lyophilized.
Figure 7A:
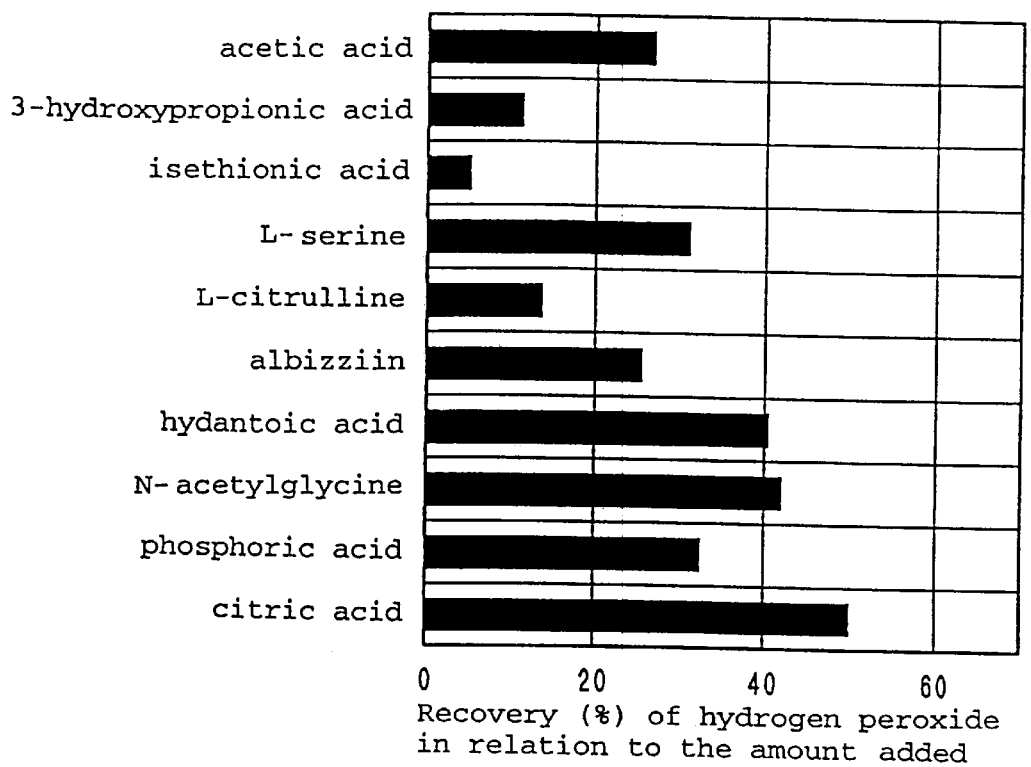
FIGS. 7(a) and 7(b) are graphs showing recovery (%) of hydrogen peroxide in relation to the amount of the hydrogen peroxide added for the cases when aqueous solution of hydrogen peroxide and various compounds of Examples of the present invention (FIG. 7(a)) and Comparative Examples (FIG. 7(b)) are impregnated in glass fiber filter paper sheets and lyophilized.

The results of the above (1), (2) and (3) are shown in FIGS. 5(a), 6(a) and 7(a).

Comparative Example 1
Comparison of hydrogen peroxide-retaining ability
The following 8 compounds:
distilled water (Wako Junyaku Kogyo K.K.),
urea (Wako Junyaku Kogyo K.K.),
methylamine (Wako Junyaku Kogyo K.K.),
monoethanolamine (Wako Junyaku Kogyo K.K.),
hydroxyurea (Wako Junyaku Kogyo K.K.),
dimethylolurea (Wako Junyaku Kogyo K.K.),
acetamide (Tokyo Kasei Kogyo K.K.), and
sodium chloride (Kokusan Kagaku K.K.),
were tested and evaluated by repeating the procedure of Example 1.

Figure 5B:
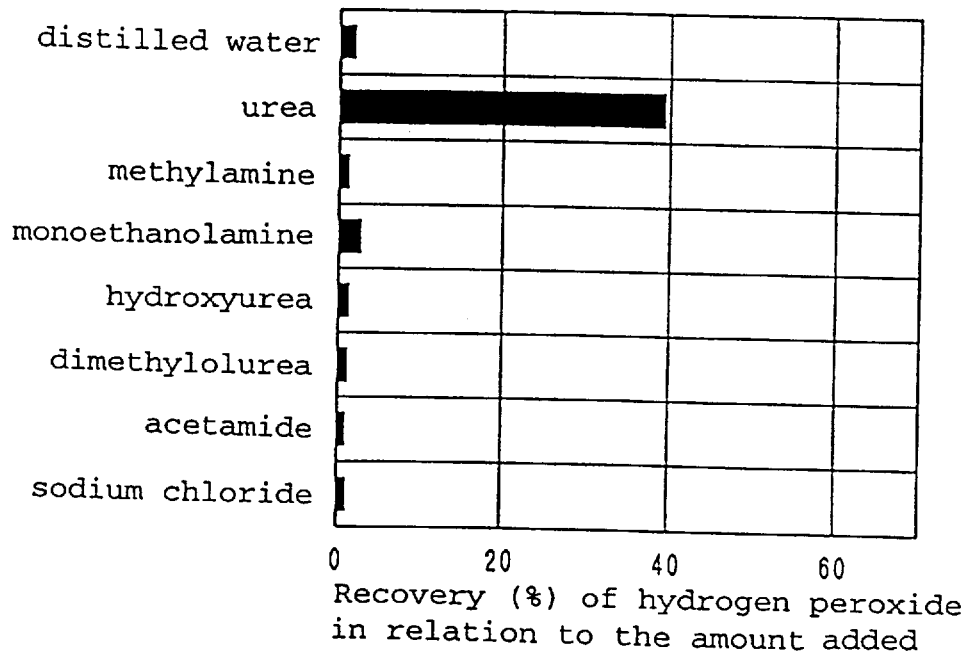
Figure 6B:
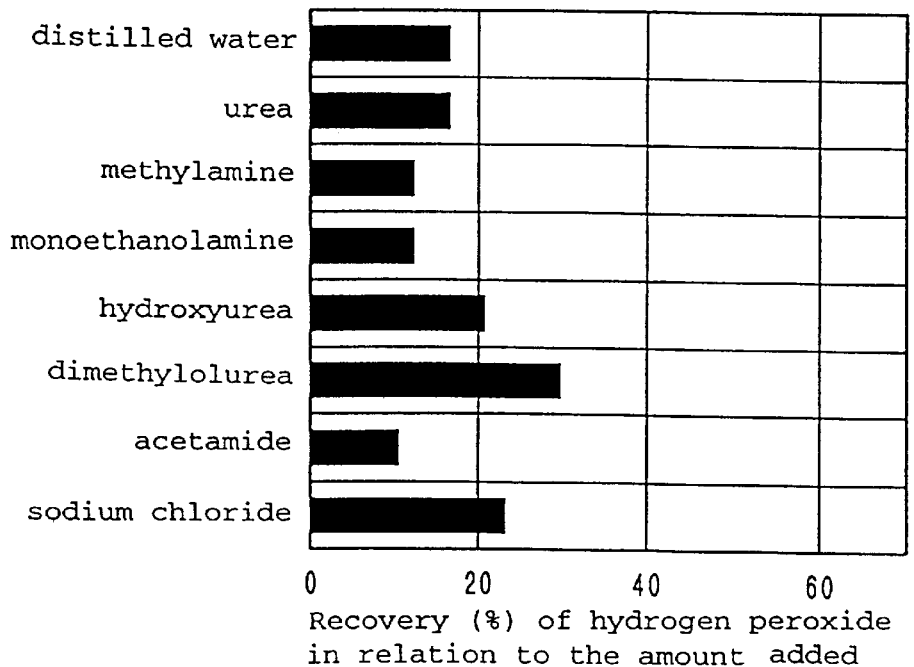
Figure 7B:
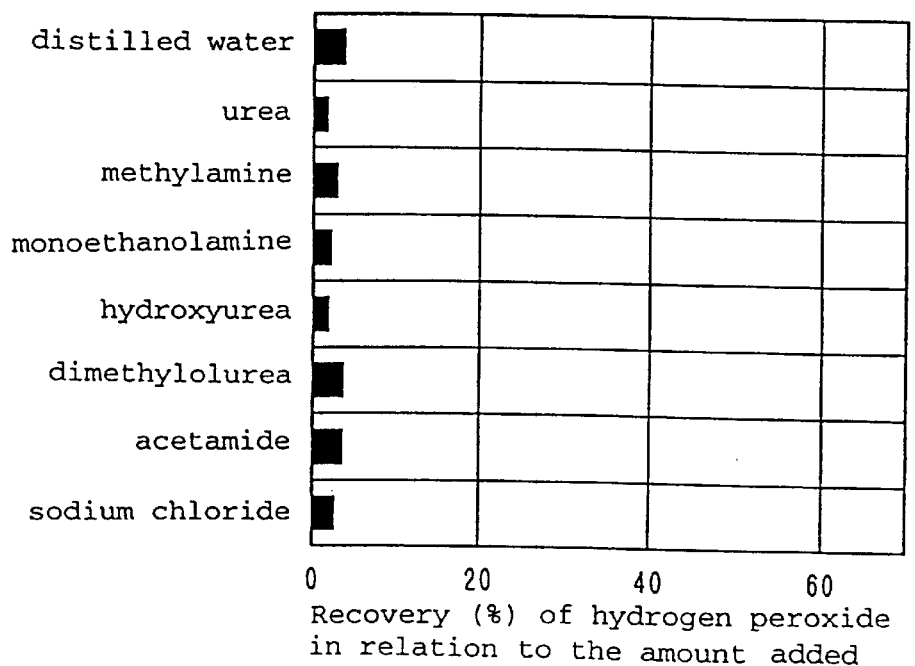

The results are shown in FIGS. 5(b), 6(b) and 7(b).

Results

In the case of the system (1) using no support, the hydrogen peroxide adducts containing acetic acid, 3-hydroxypropionic acid, isethionic acid, L-serine, L-citrulline, albizziin, hydantoic acid, N-acetylglycine, phosphoric acid, citric acid, and urea exhibited high hydrogen peroxide-retaining ability.

In the case of the system (2) wherein the reagent is loaded on a cellulose filter paper sheet, the hydrogen peroxide adducts containing acetic acid, 3-hydroxypropionic acid, L-serine, L-citrulline, albizziin, hydantoic acid, N-acetylglycine, phosphoric acid, citric acid, and dimethylolurea exhibited high hydrogen peroxide-retaining ability.

In the case of the system (3) wherein the reagent is loaded on a glass fiber filter paper sheet, the hydrogen peroxide adducts containing acetic acid, 3-hydroxypropionic acid, L-serine, L-citrulline, albizziin, hydantoic acid, N-acetylglycine, phosphoric acid, and citric acid exhibited high hydrogen peroxide-retaining ability.

It should be noted that all of the hydrogen peroxide adducts containing acetic acid, 3-hydroxypropionic acid, L-serine, L-citrulline, albizziin, hydantoic acid, N-acetylglycine, phosphoric acid, and citric acid exhibited a high hydrogen peroxide-retaining ability higher than that of the hydrogen peroxide adduct containing urea.

Example 2
Comparison of influence on the antigen-antibody reaction
[1] Preparation of a complex of anti-estradiol (E2) antibody and horseradish peroxidase (signal substance generator)

A mouse monoclonal antibody (manufactured by Mochida Pharmaceutical Co., Ltd.) which recognizes estradiol was dissolved in 100 mM sodium chloride/1 mM EDTA/60 mM triethanolamine buffer, pH 8.0 (TEA buffer solution) to a concentration of 5.3 mg/ml, and the solution was thoroughly dialyzed against TEA buffer solution purged with nitrogen gas.

To 2.2 ml of the antibody solution, 70 μl of 50 mM solution in TEA buffer of 2-iminothiolane hydrochloride (manufactured by Pierce) was added. After stirring, the solution was allowed to stand in nitrogen atmosphere at 4° C. for 1.5 hours. The solution was then thoroughly dialyzed against 100 mM sodium chloride/1 mM EDTA/100 mM phosphate buffer, pH 6.0 (EDTA-PB) purged with nitrogen gas to obtain an anti-E2 antibody having SH group introduced therein.

To 3.1 ml of horseradish peroxidase (HRPO, manufactured by Toyobo Co., Ltd.) solution adjusted to a concentration of 20 mg/ml with 100 mM sodium chloride/100 mM phosphate buffer, pH 6.0 (PB) was added 3.1 ml of 50 mM sulfoSMCC (manufactured by Pierce) with stirring at 30° C., and the reaction was allowed to take place for 20 minutes.

After the reaction, the solution was applied to a column (2.5 cm diameter×14.5 cm) of SEPHADEX G-25 (manufactured by Pharmacia) equilibrated with PB which has been purged with nitrogen gas to remove the sulfoSMCC which failed to undergo the reaction. The eluate was concentrated by using a concentrator (CENTRIPREP-10, manufactured by Amicon) to obtain maleimidated HRPO.

The concentration of the resulting maleimidated HRPO was determined by measuring absorbance at 403 nm.

To $3.3 \times 10^{-7}$ moles of maleimidated HRPO solution was added ⅕ folds in molar amount of the antibody having SH group introduced therein, and the mixture was stirred and allowed to react at 4° C. for 16 hours in nitrogen atmosphere. To this mixture was added 96 μl of 500 mM cysteamine solution in EDTA-PB, and the mixture was allowed to react at 4° C. for 60 minutes in nitrogen atmosphere. The reaction mixture was then subjected to gel permeation chromatography using ULTROGEL AcA34 (manufactured by IBF Biotechnics) equilibrated with PB purged with nitrogen gas.

The eluate fractions were measured for their absorbance at 280 nm and 403 nm, and the fractions containing the complex of the antibody and the HRPO, and which do not contain any free enzyme were collected for further concentration.

The concentrated specimen (referred to as HRPO-labeled anti-E2 antibody) was confirmed for the molecular weight by electrophoresis using Phast system (manufactured by Pharmacia), and further determined for the content of antibody and enzyme on the bases of the measurements of absorbance and enzyme activity. The thus obtained HRPO-labeled anti-E2 antibody was used in the subsequent assay as a signal substance generator.

[2] Preparation of 17β-estradiol-6-[o-carboxymethyl] oximebovine γ-globlin (E2-6CMO-γG)

6.6 mg of 17β-estradiol-6-[o-carboxymethyl]oxime (E2-6CMO, manufactured by Sigma) was dissolved in 0.66 ml of dioxane, and to this solution were added 4.62 μl of tri-n-buthylamine (manufactured by Wako Junyaku Kogyo K.K.) and 4.62 μl of isobuthylchloroformate (manufactured by Nakaraitesk K.K.). The solution was stirred at 10° C. for 30 minutes. This solution was then added to 30.32 ml of bovine γ-globlin solution (manufactured by Sigma) which had been preliminarily adjusted to 5 mg/ml with 50% aqueous solution of dioxane. The reaction solution was stirred at 10° C. for 4 hours, and in the meanwhile, the pH of the reaction solution was adjusted to the range of 8.0 to 8.5 with 0.1N sodium hydroxide solution.

The reaction solution was dialyzed against distilled water at 4° C. for 20 hours. To the reaction solution was added an equal amount of diethylether, and the solution was fully stirred. After leaving for a while, the ether layer was removed. Such extraction was repeated twice to fully remove the E2-6CMO which failed to undergo the reaction. and the aqueous layer was then dialyzed against PB to prepare the E2-6CMO-γG.

Figure 8A:
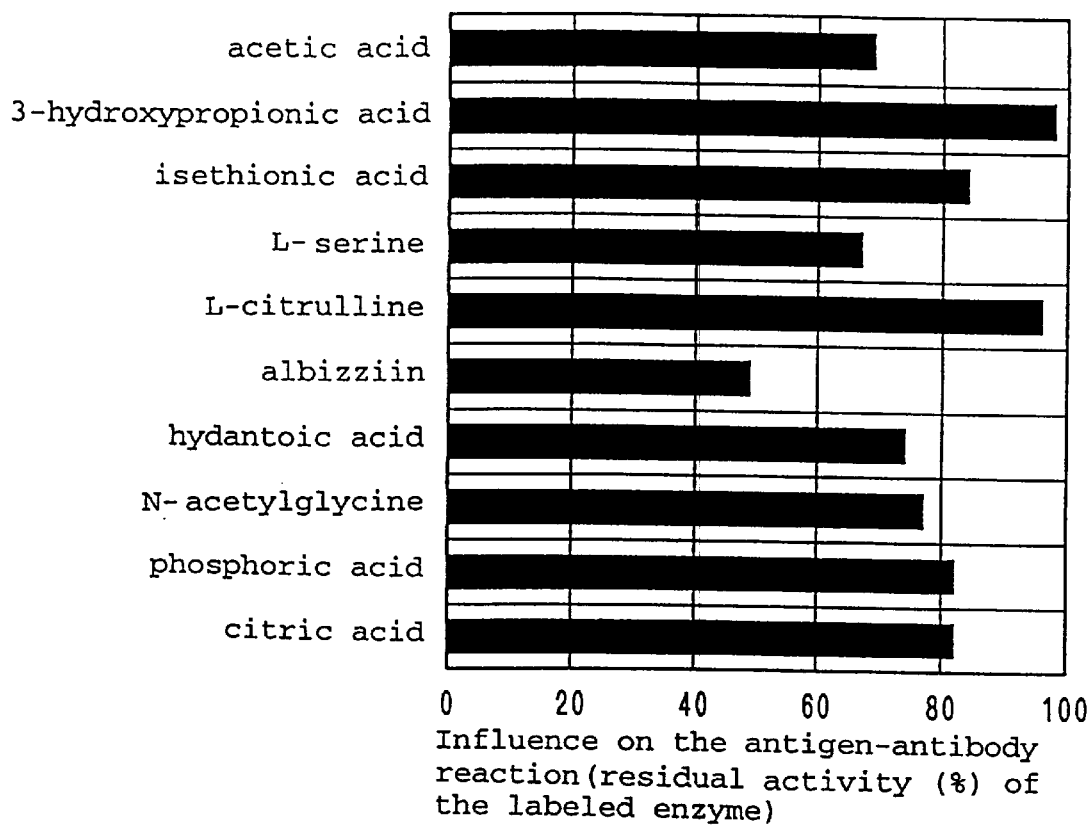
FIGS. 8(a) and 8(b) are graphs showing influence on the antigen-antibody reaction of various compounds of Examples of the present invention (FIG. 8(a)) and Comparative Examples (FIG. 8(b)). The concentration of compounds is 0.5M.

[3] Comparison of influence on the antigen-antibody reaction between the compounds To the wells of a 96 well microplate (manufactured by NUNC) was dispensed 50 μl/well of 10 μ/ml solution of the E2-6CMO-γG prepared in the above [2] in physiological saline having added phosphate buffer solution (PBS) thereto for immobilization of the E2-6CMO-γG by adsorption. After washing the wells, 100 μl/well of 0.1% normal rabbit serum (NRS) was added to the wells, and the wells were blocked by leaving the wells at 4° C. for at least 5 hours. After washing the wells, 50 μl/well of the solution prepared by adding a solution at pH 6.0 of the respective compound of the Example 1 [1] to the dilution of the HRPO-labeled anti-E2 antibody of the above [1] to a concentration of 0.25M or 0.5M was dispensed in the wells and stood at 25° C. for one hour. After washing the wells, 50 μl/well of chromogenic substrate (TMB, manufactured by ScyTek) for peroxidase was dispensed in the wells. After 10 minutes, the reaction was terminated by adding 50 μl/well of termination solution (manufactured by ScyTek), and absorbance at 450 nm was measured by ETY 96 plate reader (manufactured by Toyo Sokuki). The results are shown in FIG. 8(a).

Comparative Example 2
Comparison of influence on the antigen-antibody reaction

Figure 8B:
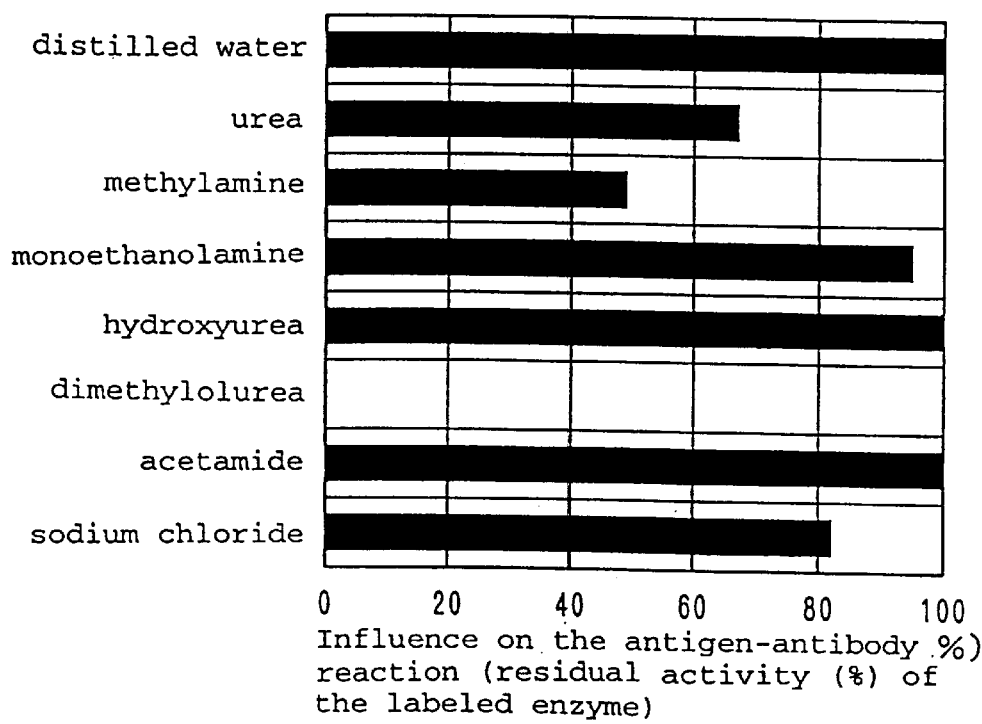

The compounds of the Comparative Example 1 [1] were tested and evaluated by repeating the procedure of Example 2. The results are shown in FIG. 8(b).
Results The compounds other than methylamine, dimethylolurea and albizziin were demonstrated to exhibit an influence on the antigen-antibody reaction smaller than that of urea.

Figure 9:
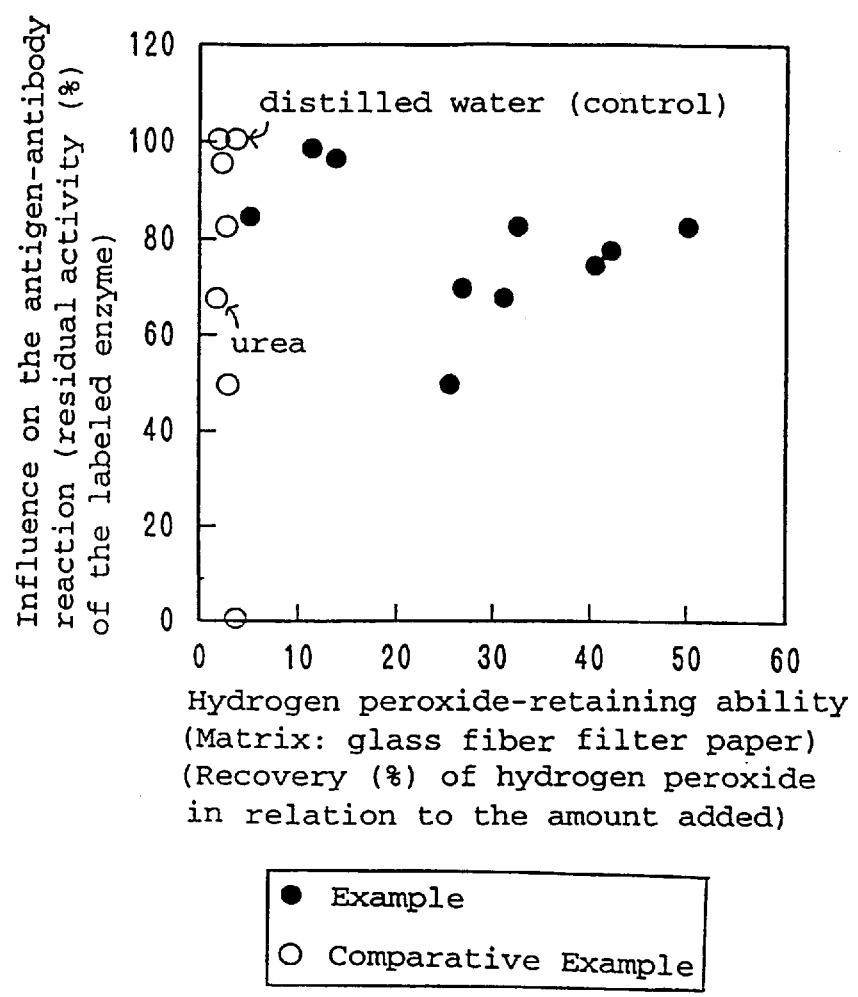
FIG. 9 is a graph showing influence on the antigen-antibody reaction of various compounds in relation to the hydrogen peroxide-retaining ability of the compounds. The concentration of compounds is 0.5M.

FIG. 9 is a graph depicted by plotting the influence on the antigen-antibody reaction of the compound in relation to the hydrogen peroxide-retaining ability of the compound. As shown in FIG. 9, acetic acid, 3-hydroxypropionic acid, L-serine, L-citrulline, hydantoic acid, N-acetylglycine, phosphoric acid, and citric acid exhibited an influence on the antigen-antibody reaction smaller than that of urea, and a hydrogen peroxide-retaining ability higher than that of urea, demonstrating the usefulness of such compounds. In the case of albizziin, it exhibited an influence on the antigen-antibody reaction larger than that of urea while its hydrogen peroxide-retaining ability was higher than that of urea. Therefore, an equivalent amount of hydrogen peroxide could be retained at a concentration lower than that of urea, and at such lower concentration of the albizziin, the influence on the antigen-antibody reaction was smaller than that of urea.

Figure 10:
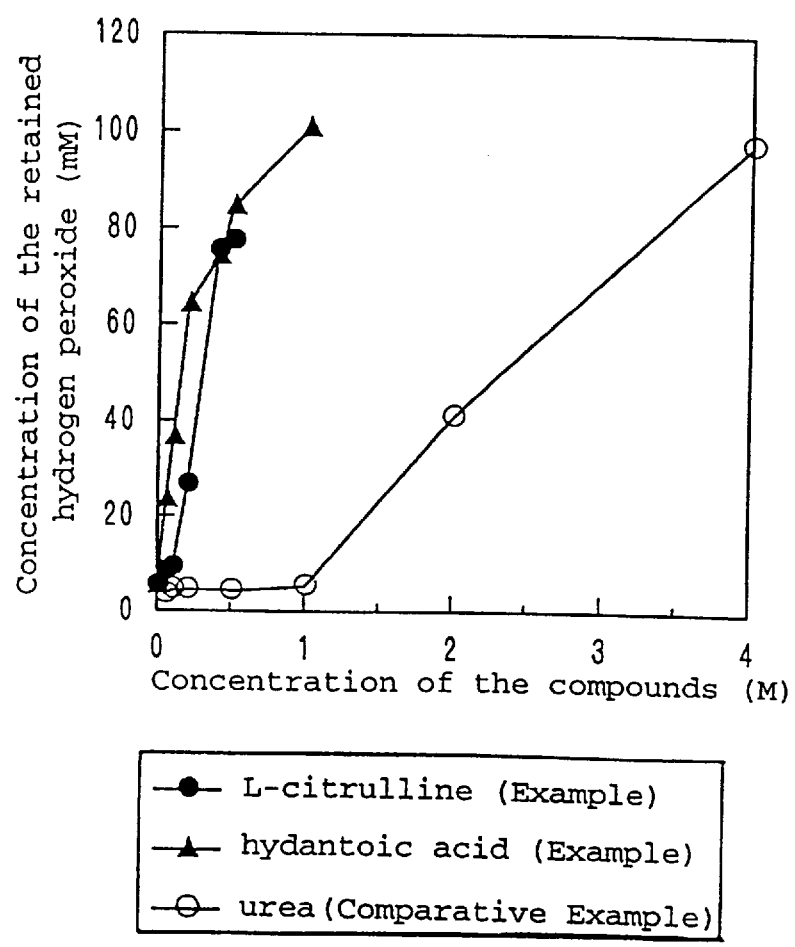
FIG. 10 is a graph showing amount of the hydrogen peroxide retained with compounds in relation to the concentration of the compounds, for different compounds. The matrix is glass fiber filter paper.

Example 3
Amount of hydrogen peroxide retained in relation to the concentration of the compound The procedure of Example 1 was repeated except that the L-citrulline and hydantoic acid were used at the concentration of 0.05M, 0.1M, 0.2M, 0.4M, 0.5M, and 1.0M, and the solutions were lyophilized in the system (3) wherein the reagent is loaded on a glass fiber filter paper sheet to thereby evaluate amount of the hydrogen peroxide retained in relation to the concentration of the compound. The results are shown in FIG. 10.

Comparative Example 3
Amount of hydrogen peroxide retained in relation to the concentration of the compound The procedure of Example 1 was repeated except that the urea was used at the concentration of 0.05M, 0.1M, 0.2M, 0.5M, 1.0M, 2.0M and 4.0M, and the solutions were lyophilized in the system (3) wherein the reagent is loaded on a glass fiber filter paper sheet to thereby evaluate amount of the hydrogen peroxide retained in relation to the concentration of the compound. The results are shown in FIG. 10.
Results In all cases of urea, L-citrulline and hydantoic acid, the amount of the hydrogen peroxide retained increased with the increase in the concentration of the compound. The hydrogen peroxide-retaining ability of both L-citrulline and hydantoic acid was approximately ten times higher than that of the urea. For example, the concentration of the compound required for retaining 40 mM hydrogen peroxide was 300 mM in the case of L-citrulline and 100 mM in the case of hydantoic acid in comparison to 2.0M in the case of urea.

Figure 11:
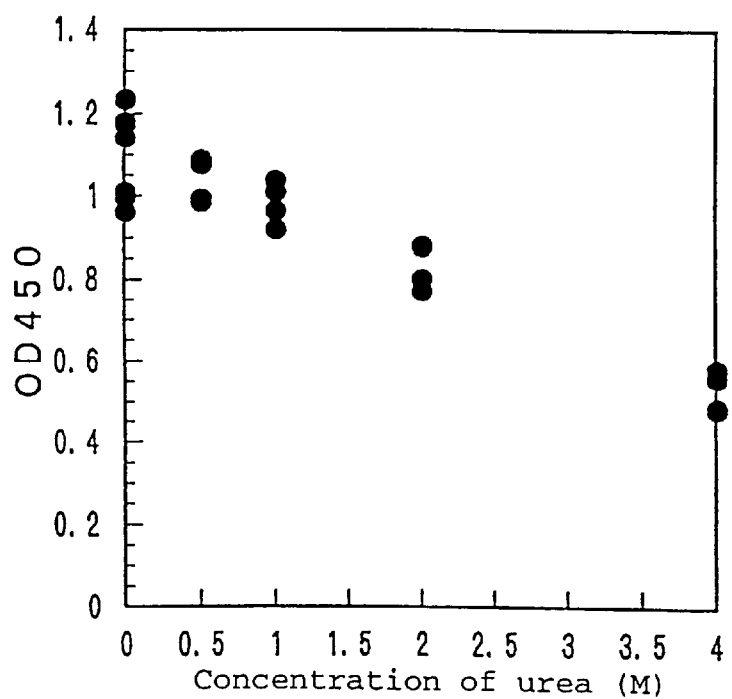
FIG. 11 is a graph showing influence on the antigen-antibody reaction of urea in relation to its concentration.

Comparative Example 4
Influence of the concentration of urea on the antigen-antibody reaction The procedure of Example 2 was repeated except that the urea was used at the concentration of 0.5M, 1.0M, 2.0M and 4.0M, and absorbance at 450 nm was measured. The results are shown in FIG. 11.
Results The absorbance at 450 nm, namely, the residual enzymatic activity decreased with the increase in the urea concentration. This result implies that the antigen-antibody reaction is inhibited to a higher degree when the urea is present at a higher concentration.

As demonstrated in Example 3 and Comparative Example 3, use of urea at a higher concentration compared to L-citrulline and hydantoic acid is required for retaining the hydrogen peroxide on the glass fiber filter paper support system, and use of the urea at such a high concentration proved to be impractical in view of the adverse effect on the antigen-antibody reaction.

Examples 4–5 and Comparative Examples 5–7

The hydrogen peroxide adducts of L-citrulline, hydantoic acid and urea were respectively located in the upstream or downstream of the electrode in the assembly of the specific binding assay device to measure estradiol (E2) in serum.
[1] Production of electrode member The upper surface and the lower surface of a transparent PET film of 0.25 mm thick were respectively screen printed with an elctroconductive carbon ink (400-CT, manufactured by Asahi Kaken K.K.), electroconductive silver paste (LS411N, manufactured by Asahi Kaken K.K.), and resist (XB-101G, manufactured by Fujikura Kasei K.K.) to produce the electrode member 22 shown in FIG. 3.

The upper surface of the PET film which constitutes the insulation board 24 was screen printed with the carbon ink to form the counter electrode (reference electrode) 34 and the terminal 34a electrically connected to the counter electrode 34. The insulation layer 36 was then formed with the insulation resist, and the ring-shaped counter electrode 34 was printed thereon with the silver paste.

Similarly, the lower surface of the PET film which constitutes the insulation board 24 was then formed with the work electrode 38 and the terminal 38a electrically connected to the work electrode 38. The insulation layer 36 was then formed with an insulation resist. (it should be noted that no printing with the silver paste was conducted on this side.)

After forming the electrodes and the insulation layers, the PET film was cut into the strip of 44 mm in length and 18 mm in width, and the center of the counter electrode 34 and the working electrode 38 was punched out to form the through hole 32. The electrode member 22 as shown in FIG. 3 was thus produced.

The parameters of the electrode member are as described below.

Electrode member 22

In Example 4 and Comparative Examples 5 and 7, the electrode as described below was employed.

Diameter of the through hole 32 (inner diameter of the work electrode 38): 2 mm

Outer diameter of the work electrode 38: 4 mm (i.e., width of the work electrode 38: 1 mm)

Inner diameter of the counter electrode (reference electrode) 34 on the upper surface: 2 mm Outer diameter of the counter electrode (reference electrode) 34: 6 mm In Example 5 and Comparative Example 6, the electrode as described below was employed.

Diameter of the through hole 32 (inner diameter of the work electrode 38): 4 mm

Outer diameter of the work 38: 7 mm (i.e., width of the work 38: 1.5 mm)

Inner diameter of the counter electrode (reference electrode) 34 on the upper surface: 4 mm Outer diameter of the counter electrode (reference electrode) 34: 8 mm Each of the thus produced electrode member 22 was checked so that the work and the counter electrode 34 were electrically independent from each other, and that the work electrode 38 and the counter electrode 34 were electrically connected to the terminal 38a and the terminal 34a, respectively.

With regard to the counter electrode 34, the silver paste electrode as described above was used for the counter electrode (reference electrode).

[2] Production of first reagent-impregnated member 18 (the member having impregnated therein the signal substance generator-electronic mediator, namely, the horseradish peroxidase-labeled anti-E2 antibody and N,N,N',N'-tetrakis (2'-hydroxyethyl) -p-phenylenediamine dichloride (THEPD))

A dilution of the horseradish peroxidase-labeled anti-E2 antibody prepared in Example 2 [1] and THEPD (final concentration, 2 mM) with 5% normal rabbit serum (NRS) /10% lactose/0.1M NaCl-containing 0.01M phosphate buffer solution, pH 7.4 was prepared.

The resulting solution was spotted onto the round-shaped sheets of 12 mm diameter punched out from the TWEEN20-treated glass fiber filter paper prepared in Example 1 [2] at 140 µl/sheet, and the sheets were lyophilized. The first reagent-impregnated member 18 (the member having impregnated therein the signal substance generator-electronic mediator) was thus prepared.

[3] Production of second reagent-impregnated member 20

As will be described in the following description, a buffer solution containing hydrogen peroxide and hydantoic acid was prepared in Examples 4 and 5; and a buffer solution containing hydrogen peroxide and urea was prepared in Comparative Examples 5 and 6. A buffer solution was used in Comparative Examples 7. The solution was spotted onto the round-shaped sheets of 12 mm diameter punched out from the TWEEN20-treated glass fiber filter paper prepared in Example 1 [2] at 140 µl/sheet, and the sheets were lyophilized. The second reagent-impregnated member 20 was thus prepared.

[4] Production of antigen-immobilized flow path member 26 (hapten-immobilized membrane, namely, E2-6CMO-γG-immobilized porous cellulose-blended ester membrane)

The E2-6CMO-γG prepared in Example 2 [2] was dissolved in PBS to a concentration of 2.0 mg/ml. In this solution were immersed 1000 sheets of round-shaped porous membranes of 13 mm diameter punched out from porous cellulose-blended ester membrane (pore size, 8.0 µm; purchased from Millipore Japan) in a beaker at 25° C. for 30 minutes under shaking.

After wiping the moisture of the porous membrane sheets with a filter paper, the porous membrane sheets were dried at a reduced pressure for overnight to prepare the antigen-immobilized flow path member 26.

[5] Production of absorption member 28 (dried matrix wherein hydrogen peroxide adduct has been impregnated)

Round-shaped sheets of 12 mm diameter punched out from a chromatography filter paper (17 Chr, Whatman) were prepared. In the case of Comparative Example 7, the sheets were impregnated with the solution as will be described later and lyophilized to prepare the dried matrix 28 having a hydrogen peroxide adduct impregnated therein.

[6] Production of specific binding assay device

The thus produced members were assembled as described below to produce the specific binding assay device shown in FIGS. 2 and 4.

First, the filter paper of the absorption member 28 having disposed thereon the seal member 28a (having a thickness of 25 µm; and a diameter of 4 mm in the case of Example 4 and Comparative Examples 5 and 7, and 7 mm in the case of Example 5 and Comparative Example 6) was disposed on and in alignment with the bottom board 30 made of an acrylic resin. The antigen-immobilized flow path member 26 (hapten-immobilized membrane) was disposed on and in alignment with the absorption member 28. It should be noted that in Comparative Example 7, a dried matrix having a hydrogen peroxide adduct impregnated therewith was used for the absorption member 28.

The electrode member 22 was then disposed on the antigen-immobilized flow path member 26 with the side of the work electrode 38 in contact with the antigen-immobilized flow path member 26 such that the through hole 32 was in alignment with the antigen-immobilized flow path member 26.

Next, the second reagent-impregnated member 20 was disposed on the electrode member 22 such that the through hole 32 was in alignment with the second reagent-impregnated member 20. The seal member 20a of PET (having a thickness of 25 µm and a diameter of 10 mm) was adhered in the center of the upper surface of the second reagent-impregnated member 20. The first reagent-impregnated member (the member having impregnated therein the signal substance generator-electronic mediator) 18 was then disposed on the second reagent-impregnated member 20.

Figure 12A:
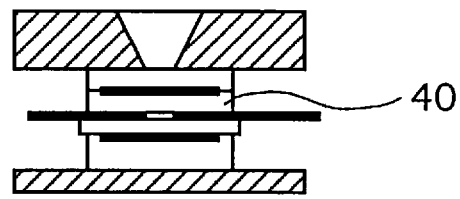
FIGS. 12(a) and 12(b) are schematic views of the specific binding assay devices in which a dried matrix having hydrogen peroxide-hydantoic acid aqueous solution impregnated therein has been arranged in the upstream side of the device (FIG. 12(a)) and in the downstream side of the device (FIG. 12(b)).
Figure 12B:
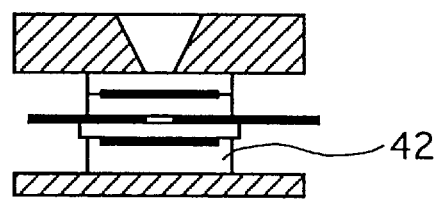

The top cover 16 made of an acrylic resin provided with the sample inlet port 16a of 3 mm in diameter was then disposed on the first reagent-impregnated member 18 such that the sample inlet port 16a was in alignment with the through hole 32. The top cover 16 and the bottom board 30 were adjusted such that tapped holes on four corners of the top cover 16 were in alignment with those of the bottom board 30, and the top cover 16 was screwed onto the bottom board 30. The specific binding assay device adapted for measuring the concentration of estradiol as shown in FIGS. 2 and 4 was thus produced. The arrangement of the reagent impregnated member are illustrated by the sectional views of the specific binding assay device of FIG. 12. FIG. 12(a) is the view in which the dried matrix 40 having hydrogen peroxide-hydantoic acid aqueous solution impregnated and lyophilized therein is arranged in the upstream side of the device. FIG. 12(b) is the view in which the dried matrix 42 having hydrogen peroxide-urea aqueous solution impregnated and lyophilized therein is arranged in the downstream side of the device.

[7] Measurement of E2 in serum

In the electrode member 22 of the thus produced specific binding assay device, the terminal 34a of the counter electrode 34 was connected to the terminal of the counter electrode (reference electrode) of the current-measuring circuit, and the terminal of the work electrode of the current-measuring circuit was connected to the terminal 38a of the work electrode 38. The data from the current-measuring circuit were transmitted to the computer for further data analysis through a data collection board, AT-MIO-16X manufactured by National Instrument.

E2 of standard concentrations was added to a pooled serum (code 3SH027, manufactured by Scantibodies Laboratory) to prepare serum samples with the E2 concentration of 0.1 ng/ml and 100 ng/ml. 200 μl of each of the E2-containing serum samples was introduced into the sample introduction unit from the sample inlet port 16a of the acrylic resin top cover 16 of the specific binding assay device.

After the introduction of the sample, potential of the work electrode was adjusted to −150 mV in relation to the counter electrode (reference electrode), and the current value was recorded.

Example 4

Measurement of estradiol (E2) in serum by the specific binding assay device wherein hydrogen peroxide-hydantoic acid is arranged in the upstream of the electrode (which is the case of the present invention)

500 mM hydrogen peroxide/100 mM hydantoic acid (adjusted to pH 6.0 with KOH)/160 U/ml heparin/0.1M NaCl was prepared, and this solution was used in the production of the second reagent-impregnated member described in the above [3]. The device described in the above [6] was assembled and the measurement described in the above [7] was conducted.

Figure 13:
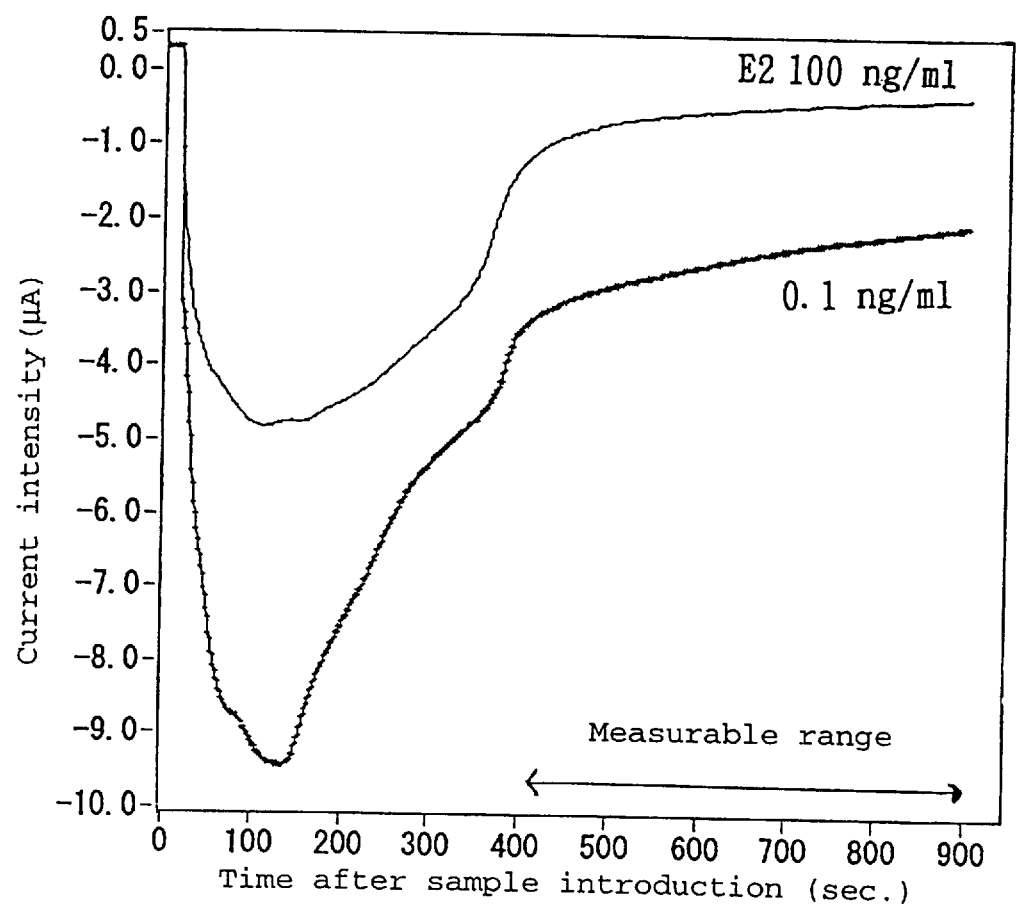
FIG. 13 is a graph showing current intensity in relation to lapse of time when the dried matrix having hydrogen peroxide-hydantoic acid aqueous solution impregnated therein is arranged in the upstream side of the device.

The results are shown in FIG. 13.

Comparative Example 5

Measurement of estradiol (E2) in serum by the specific binding assay device wherein hydrogen peroxide-urea is arranged in the upstream of the electrode 500 mM hydrogen peroxide/2.0M urea/160 U/ml heparin/0.1M NaCl was prepared, and this solution was used in the production of the second reagent-impregnated member described in the above [3]. The device described in the above [6] was assembled and the measurement described in the above [7] was conducted.

Results

Current flow in correspondence with the E2 concentration was observed in the case of Example 4, while the measurement could not be conducted in the case of Comparative Example 5 because of clogging of the hapten-immobilized membrane due to the high concentration of the urea. As demonstrated in Example 3 and Comparative Example 3, 100 mM hydantoic acid (Example 4) and 2.0M urea (Comparative Example 5) retain substantially the same amount of hydrogen peroxide. The provision of urea of such a high concentration in the upstream of the electrode, however, proved to be inadequate since flow of the sample solution was blocked.

Example 5

Measurement of estradiol (E2) in serum by the specific binding assay device wherein hydrogen peroxide-hydantoic acid is arranged in the upstream of the electrode (which is the case of the present invention)

25 mM hydrogen peroxide/100 mM hydantoic acid (adjusted to pH 6.0 with KOH)/160 U/ml heparin/0.1M NaCl was prepared, and this solution was used in the production of the second reagent-impregnated member described in the above [3]. The device described in the above [6] was assembled and the measurement described in the above [7] was conducted.

Figure 14:
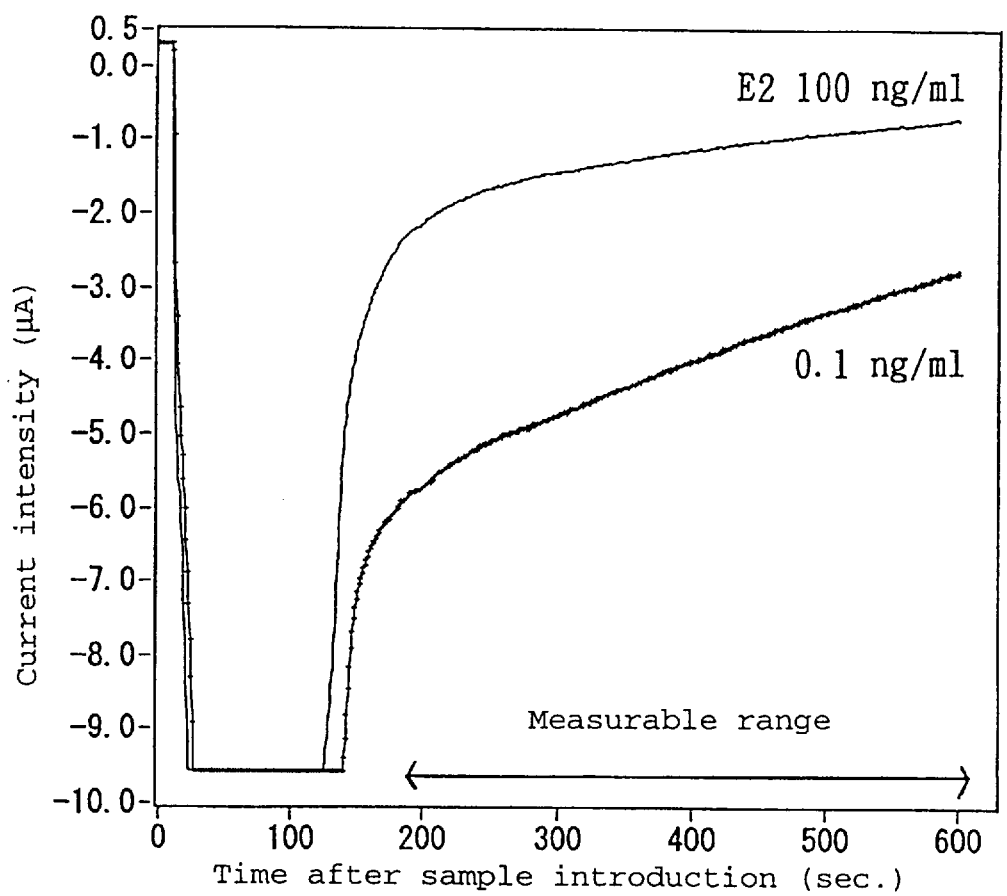
FIG. 14 is a graph showing current value in relation to lapse of time when the dried matrix having hydrogen peroxide-hydantoic acid aqueous solution impregnated therein is arranged in the upstream side of the device.

The results are shown in FIG. 14.

Comparative Example 6

Measurement of estradiol (E2) in serum by the specific binding assay device wherein hydrogen peroxide-urea is arranged in the upstream of the electrode 500 mM hydrogen peroxide/2.0M urea/160 U/ml heparin/0.1M NaCl was prepared, and this solution was used in the production of the second reagent-impregnated member described in the above [3]. The device described in the above [6] was assembled and the measurement described in the above [7] was conducted.

Figure 15:
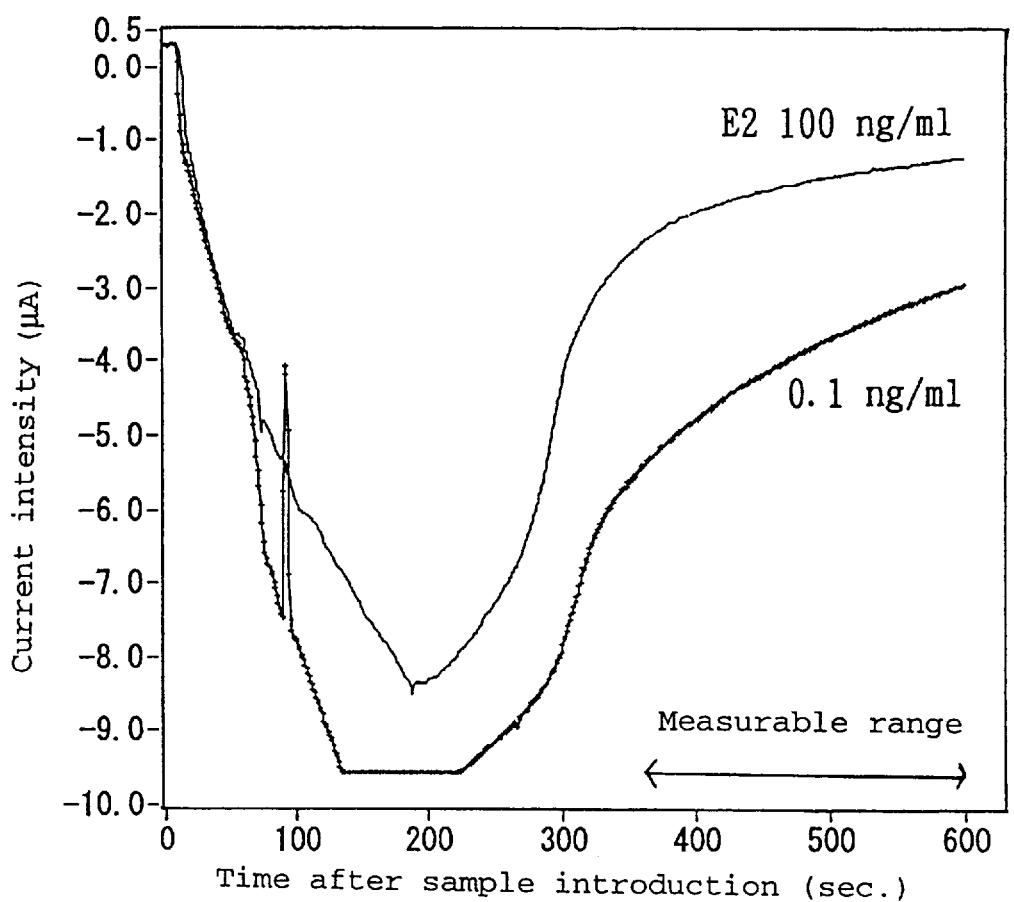
FIG. 15 is a graph showing current value in relation to lapse of time when the dried matrix having hydrogen peroxide-urea aqueous solution impregnated therein is arranged in the upstream side of the device.

The results are shown in FIG. 15.

Results

Comparison between hydantoic acid and urea was conducted by optimizing the concentration of the hydrogen peroxide, hydantoic acid, and urea, and using the MEDIA device with the through hole 32 of the electrode member dilated to 4 mm (EX5, CEX6) from that of 2 mm (EX4, CEX5) for accelerating the impregnation of the hapten-immobilized membrane with the sample solution. In the case of hydantoic acid (Example 5), a stable current flow in correspondence with the E2 concentration was observed after as short as about 200 seconds. On the other hand, in the case of urea (Comparative Example 6), rise of the current flow was slow and the current measurements were unstable in spite of such a large through hole 32.

Comparative Example 7

Measurement of estradiol (E2) in serum by the specific binding assay device wherein hydrogen peroxide-urea is arranged in the downstream of the electrode (which is the case corresponding to the prior art)

0.01M phosphate buffer solution containing 0.1M NaCl, pH 7.4 was prepared, and this solution was used in the production of the second reagent-impregnated member described in the above [3].

Hydrogen peroxide (Wako Junyaku Kogyo K.K.) and urea (Wako Junyaku Kogyo K.K.) were dissolved in distilled water to 1.0M hydrogen peroxide/4.0M urea solution. 100 μl of this solution was spotted onto the round-shaped filter paper sheets described in the above [5], and the sheets were lyophilized to prepare the dried matrix having urea adduct of hydrogen peroxide impregnated therein.

The device described in the above [6] was assembled and the measurement described in the above [7] was conducted.

Figure 16:
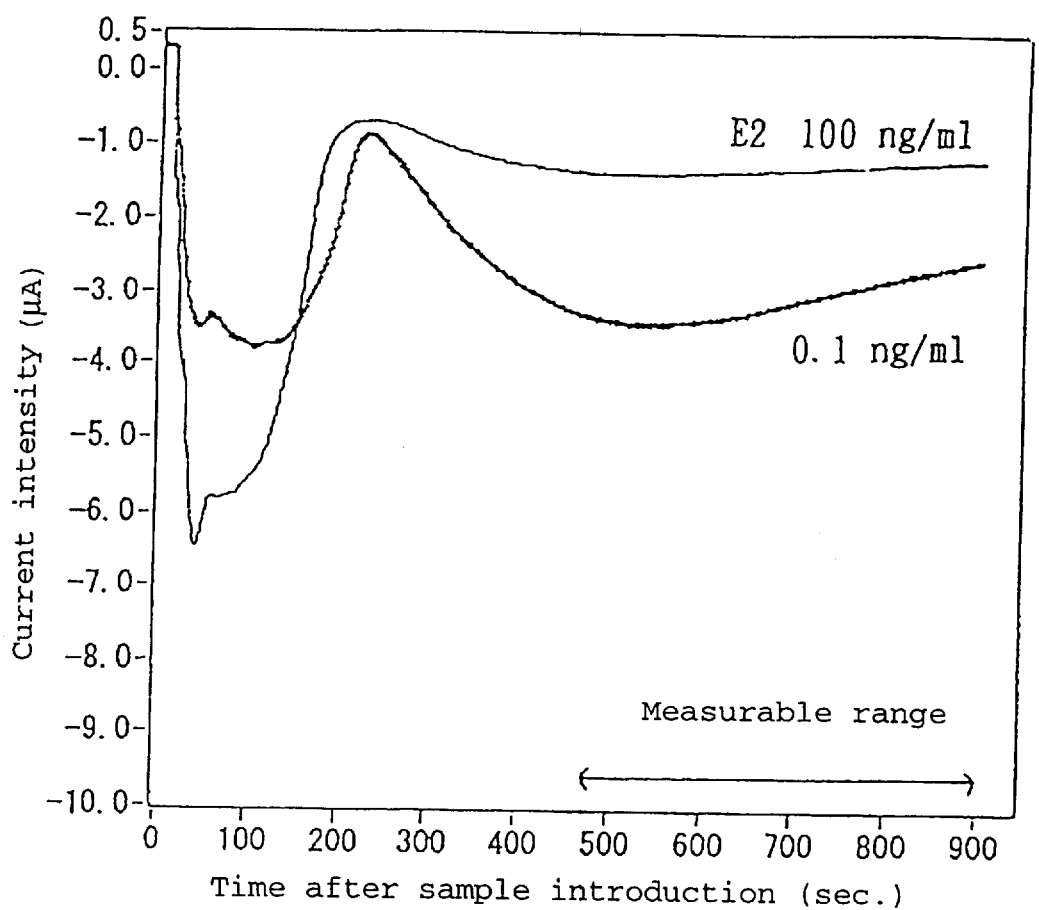
FIG. 16 is a graph showing current value in relation to lapse of time when the dried matrix having hydrogen peroxide-urea aqueous solution impregnated therein is arranged in the downstream side of the device.

The results are shown in FIG. 16.

Results

In the case of hydantoic acid adduct with hydrogen peroxide being arranged in the side of the upstream (Example 5, FIG. 14), a rise in the current flow as well as a stable current flow were observed after a short while, allowing the measurement to be completed in a short period in contrast to the case of urea adduct with hydrogen peroxide being arranged in the side of the downstream in order to avoid the adverse effect of urea to antigen-antibody reaction and liquid flow (Comparative Example 7, FIG. 16).

In the case of Comparative Example 7 (FIG. 16) wherein urea adduct with hydrogen peroxide was arranged in the downstream of the electrode, when the sample solution was introduced in the device at time 0 second, current flow (reductive current in one direction as shown in FIG. 16) induced by the passage by the work electrode of the dissolved enzyme-labeled antibody, electronic mediator and the like was observed for a short while, and the current value decreased once after about 200 seconds. When the sample solution reached the lowermost absorption member to dissolve the impregnated hydrogen peroxide, the dissolved hydrogen peroxide diffused in backward direction, and the current value started increasing after about 250 seconds. It was after about 600 seconds that the difference in the current value between the case wherein E2 was at 100 ng/ml and the case wherein E2 was at 0.1 ng/ml reached the maximum.

On the other hand, in the case of FIG. 14 wherein the hydantoic acid adduct with hydrogen peroxide was arranged in the upstream of the electrode, when the sample solution was introduced into the device at time 0 second, current flow (reductive current in one direction as shown in FIG. 14) induced by the passage by the work electrode of the dissolved enzyme-labeled antibody, electronic mediator and the like was observed for a short while, and a stable difference in the current value between the case wherein E2 was at 100 ng/ml and the case wherein E2 was at 0.1 ng/ml appeared after as short as about 200 to 300 seconds.

Similar results were obtained when the hydantoic acid was replaced with L-citrulline, phosphoric acid, citric acid, acetic acid, or N-acetylglycine.

Examples 6–9 and Comparative Example 8

In order to determine the compounds suitable for constituting the hydrogen peroxide adduct for use in the present invention, various compounds were tested and evaluated for their hydrogen peroxide-retaining ability.

Example 6

Comparison of hydrogen peroxide-retaining ability

The compounds shown in Table 1 were respectively dissolved in distilled water to prepare 200 mM solutions of the compounds. pH of the solutions was adjusted to about 6.0 by the addition of aqueous HCl solution or aqueous NaOH solution. These solutions and hydrogen peroxide (Wako Junyaku Kogyo K.K.) were used to prepare the solutions containing 100 mM hydrogen peroxide and 100 mM compound.

Each solution was dispensed in glass vials of 3.0 ml volume in 100 μl portions, and lyophilized. After the lyophilization, 1.0 ml of distilled water was added to the vial to reconstitute the lyophilized component, and the concentration of the hydrogen peroxide in the reconstituted solution was quantitated by PoroXOquant™ Quantitative Peroxide Assay kit (manufactured by PIERCE) to thereby calculate the recovery (%) of the hydrogen peroxide in relation to the amount of hydrogen peroxide that had been added before the lyophilization. The results are shown in Table 1.

TABLE 1

| Compound | Recovery (%) of $H_2O_2$ in relation to the amount added |
|---|---|
| acetic acid | 39.3 |
| glycolic acid | 30.5 |
| propionic acid | 2.5 |
| pyruvic acid | 12.8 |
| 3-hydroxypropionic acid | 30.5 |
| DL-lactic acid | 35.9 |
| DL-glyceric acid | 38.0 |
| 2,2-bis(hydroxymethyl)propionic acid | 43.7 |
| glucuronic acid | 41.7 |
| gluconic acid | 46.5 |
| glucoheptonic acid | 47.6 |
| oxalic acid | 56.7 |
| malonic acid | 62.6 |
| methylmalonic acid | 57.0 |
| succinic acid | 47.6 |
| oxaloacetic acid | 23.4 |
| methylsuccinic acid | 48.4 |
| 2,2-dimethylsuccinic acid | 2.7 |
| maleic acid | 49.6 |
| fumalic acid | 2.8 |
| citraconic acid | 18.9 |
| acetylenedicarboxylic acid | 3.4 |

TABLE 1-continued

| Compound | Recovery (%) of $H_2O_2$ in relation to the amount added |
|---|---|
| (S)-(−)-malic acid | 57.6 |
| DL-malic acid | 59.7 |
| (S)-(+)-citramalic acid | 58.6 |
| L-(+)-tartaric acid | 56.5 |
| DL-tartaric acid | 44.3 |
| glutaric acid | 53.5 |
| diglycolic acid | 56.2 |
| 2-ketoglutaric acid | 7.2 |
| 3-ketoglutaric acid | 3.1 |
| 3-methylglutaric acid | 30.2 |
| 3-hydroxy-3-methylglutaric acid | 47.1 |
| adipic acid | 3.5 |
| mucic acid | 42.2 |
| pimelic acid | 41.7 |
| suberic acid | 23.8 |
| citric acid | 53.6 |
| trans-aconit acid | 61.8 |
| 1,3,5-pentanetricarboxylic acid | 63.4 |
| meso-butane-1,2,3,4-tetracarboxylic acid | 60.6 |
| cis-1,2-cyclohexanedicarboxylic acid | 20.8 |
| trans-1,2-cyclohexanedicarboxylic acid | 63.7 |
| 1,4-cyclohexanedicarboxylic acid | 53.5 |
| o-phthalic acid | 60.6 |
| isopthalic acid | 54.1 |
| terephthalic acid | 5.2 |
| 4-hydroxyphthalic acid | 43.6 |
| 4-hydroxyisophthalic acid | 54.1 |
| 5-hydroxyisophthalic acid | 31.9 |
| 4-hydroxyphenylacetic acid | 52.4 |
| vanillic acid | 40.0 |
| guaiacol sulfonic acid | 2.2 |
| hydantoic acid | 28.6 |
| L-alanine | 1.3 |
| L-serine | 29.6 |
| L-threonine | 15.6 |
| L-glutamic acid | 61 |
| L-citrulline | 37.7 |
| D(+)-glucose | 25.6 |
| galactose | 29.6 |
| maltose | 25 |
| saccharose | 34 |
| lactose | 23.1 |
| trehalose | 22.8 |
| mannitol | 0.2 |
| N-acetyl-D(+)-glucosamine | 19.1 |
| L-(+)-ascorbic acid | 0.4 |
| N-acetylglycine | 60.7 |
| picolic acid | 25.6 |
| N-(2-acetamide)iminodiacetic acid | 59.9 |
| L-cysteic acid | 45.6 |
| taurine | 0.5 |
| phosphoric acid | 39.6 |
| creatinine | 0.4 |

Example 7

Comparison of hydrogen peroxide-retaining ability

The compounds shown in Table 2 were evaluated for their hydrogen peroxide-retaining ability by repeating the procedure of Example 6 except that the compounds were used at the concentration of 0.25% and/or 2.0% as shown in Table 2.

The results are shown in Table 2.

TABLE 2

| Compound | Recovery (%) of $H_2O_2$ in relation to the amount added |
|---|---|
| 0.25% sodium chondroitin sulfate | 1.4 |
| 0.25% sodium arginate 100–150 cP | 2.4 |
| 0.25% polyethylene glycol 6,000 | 0.1 |
| 0.25% dextran | 0.4 |
| 0.25% sodium carboxymethyl cellulose | 1.3 |
| 0.25% polyacrylic acid | 7.8 |
| 2.0% sodium chondroitin sulfate | 14.7 |
| 2.0% polyethylene glycol 6,000 | 0.4 |

Comparative Example 8

Comparison of hydrogen peroxide-retaining ability

The compounds shown in Table 3 were evaluated for their hydrogen peroxide-retaining ability by repeating the procedure of Example 6.

The results are shown in Table 3.

TABLE 3

| Compound | Recovery (%) of $H_2O_2$ in relation to the amount added |
|---|---|
| distilled water (control) | 0.0 |
| sodium chloride | 0.0 |
| urea | 0.0 |
| ammonium carbamate | 0.0 |
| guanidine chloride | 0.0 |

Results

All of the compounds shown in Table 1 exhibited hydrogen peroxide-retaining ability to some extent. The solution having a pH value in the range of at least 4–9 exhibited the ability. The hydrogen peroxide-retaining ability were found even when the lyophilizates were stored at 45° C. for 24 hours or at 4° C. for 6 months. The polymers shown in Table 2 also exhibited hydrogen peroxide-retaining ability, and the hydrogen peroxide-retaining ability exhibited were higher when the concentration of the compound was higher. On the contrary, urea which had been known to posses the hydrogen peroxide-retaining ability exhibited hardly any hydrogen peroxide-retaining ability at a concentration equivalent to those (100 mM) of the compounds of Example 6 (Table 3).

With regard to correlation between the structure of the compounds and their hydrogen peroxide-retaining ability, the following tendencies were found.

(1) At least the compounds having hydroxyl group, carboxyl group, phosphate group, or sulfate group exhibited the hydrogen peroxide-retaining ability. Among these, the compounds having carboxyl group or phosphate group exhibited higher hydrogen peroxide-retaining ability.

(2) The compounds having two or more types of functional groups, for example, the compounds having both carboxyl group and hydroxyl group exhibited higher hydrogen peroxide-retaining ability.

(3) The compounds having two or more functional groups exhibited higher hydrogen peroxide-retaining ability. For example, the compounds having two or more carboxyl groups exhibited higher hydrogen peroxide-retaining ability than the compounds having one carboxyl group.

As shown in Table 4 for the compounds having two carboxyl groups, such compounds exhibited the hydrogen peroxide-retaining ability irrespective of the chain length of the molecule. The compounds having double bound or triple bond and the compounds wherein the functional group is present on the cyclohexane ring or the benzene ring also exhibited the hydrogen peroxide-retaining ability. Consequently, all compounds exhibited a hydrogen peroxide-retaining ability higher than the urea used in the Comparative Example, and they were suitable as a reagent for adduct of hydrogen peroxide.

TABLE 4

| Compound | characteristic structure | Recovery (%) of $H_2O_2$ in relation to the amount added |
|---|---|---|
| oxalic acid | HOOC—COOH | 56.7 |
| malonic acid | HOOC—$CH_2$—COOH | 62.6 |
| succinic acid | HOOC—$(CH_2)_2$—COOH | 48.4 |
| gluraric acid | HOOC—$(CH_2)_3$—COOH | 53.5 |
| adipic acid | HOOC—$(CH_2)_4$—COOH | 3.5 |
| pimelic acid | HOOC—$(CH_2)_5$—COOH | 41.7 |
| suberic acid | HOOC—$(CH_2)_6$—COOH | 23.8 |
| maleic acid | double bond | 49.6 |
| fumaric acid | double bond | 2.8 |
| ctraconic acid | double bond | 18.9 |
| trans-aconit acid | double bond | 61.8 |
| acetylenedicarboxylic acid | triple bond | 3.4 |
| cis-1,2-cyclohexane-dicarboxylic acid | cyclohexane | 20.8 |
| trans-1,2-cyclohexane-dicarboxylic acid | cyclohexane | 63.7 |
| 1,4-cyclohexane-dicarboxylic acid | cyclohexane | 53.5 |
| o-phthalic acid | benzene ring | 60.6 |
| isopthalic acid | benzene ring | 51.1 |
| terephthalic acid | benzene ring | 5.2 |
| 4-hydroxyphthalic acid | benzene ring | 43.6 |
| 4-hydroxyisophthalic acid | benzene ring | 54.1 |
| 5-hydroxyisophthalic acid | benzene ring | 31.9 |
| 4-hydroxyphenylacetic acid | benzene ring | 52.4 |
| vanillic acid | benzene ring | 40.0 |
| guaiacol sulfonic acid | benzene ring | 2.2 |

Example 8

Comparison of hydrogen peroxide-retaining ability

The procedure of Example 6 was repeated by using the compounds shown in Table 5 to prepare solutions containing 100 mM hydrogen peroxide and 100 mM compound.

Round-shaped sheets of 10 mm diameter punched out from a chromatography filter paper (514A, manufactured by Advantech-Toyo K.K.) were placed side by side on a bat, and 25 µl/sheet of the solution was spotted on the filter paper sheets. The sheets were then lyophilized.

The thus lyophilized filter paper was sealed in an aluminum bag with a desiccant and stored at 4° C. or 45° C. for 24 hours. Each filter paper was immersed in 3.0 ml of 0.1M phosphoric acid/0.1M sodium chloride buffer, pH 6.0, and shaken at 150 rpm for 1 hour. The supernatant was then collected. The hydrogen peroxide was quantitated by repeating the procedure of Example 6 to calculate the recovery (%) in relation to the amount of hydrogen peroxide that had been added before the lyophilization. The results are shown in Table. 5.

TABLE 5

| Compound | Recovery (%) of $H_2O_2$ in relation to the amount added | |
|---|---|---|
| | immediately after lyophilization | After 24 hr. at 45° C. |
| hydantoic acid | 82.9 | 33.9 |
| acetic acid | 76.1 | 59.7 |
| DL-lactic acid | 51.8 | 46.2 |
| malonic acid | 56.8 | 45.4 |
| L-(+)-tartaric acid | 57.2 | 39.2 |
| glutaric acid | 66.1 | 28.3 |
| pimelic acid | 82.0 | 56.2 |
| citric acid | 85.4 | 46.9 |

Results

All of the compounds shown in Table 5 exhibited considerable hydrogen peroxide-retaining ability. Furthermore, the hydrogen peroxide-retaining ability of these compounds were retained even when the lyophilizates were stored at 45° C. for 24 hours, indicating the high storage stability of the hydrogen peroxide adduct prepared by using such compounds.

Example 9

Measurement of estradiol (E2) in plasma by the specific binding assay device

Figure 17:
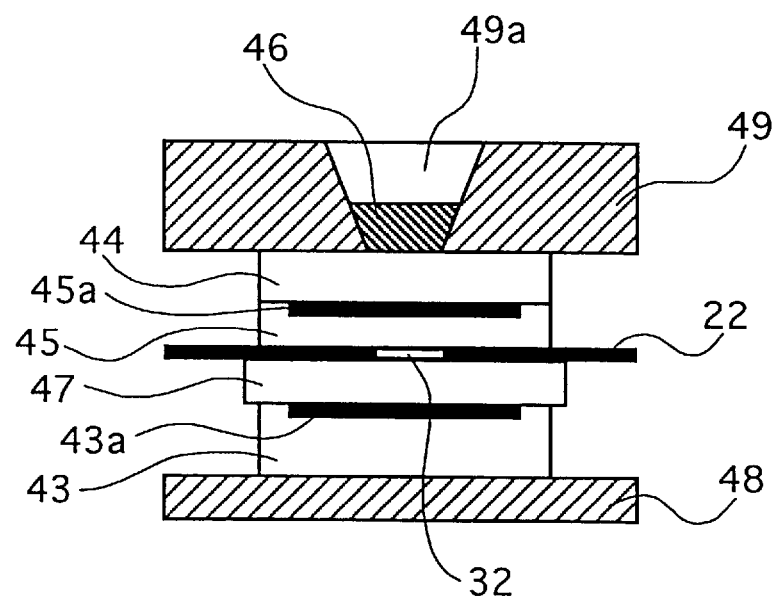
FIG. 17 is a schematic view of the assay device used in Example 9 for measuring estradiol (E2).

Estradiol (E2) in plasma was measured by using the dried matrix having hydrogen peroxide adduct impregnated therein prepared in Example 8 for the absorption member. The assay device prepared is schematically shown in FIG. 17. In the assay device, the absorption member 43 was arranged in the downstream of the electrode.

[1] Production of absorption member 43 (the dried matrix having hydrogen peroxide adduct impregnated therein)

The dried matrix having hydrogen peroxide adduct impregnated therein prepared in Example 8 was used for the absorption member 43.

[2] Production of glass fiber filter paper treated with a surfactant (TWEEN 20)

Glass fiber filter paper treated with a surfactant (TWEEN 20) was prepared by repeating the procedure of Example 1 [2] using a glass fiber filter paper (GF/C, manufactured by Whatman). Round-shaped sheets of 10 mm diameter were punched out from the thus prepared Surfactant (TWEEN 20)-treated glass fiber filter paper, and used for first layer 44 and second layer 45.

[3] Production of dried reagent 46 (signal substance-electron mediator-impregnated member: a dried matrix having HRPO-labeled anti-E2 antibody and N,N,N',N'-tetrakis-(2'-hydroxyethyl)-p-phenylenediamine dichloride (THEPD) impregnated therein)

Dilution of the HRPO-labeled anti-E2 antibody prepared in Example 2 [1] and THDPD (final concentration, 9 mM) with 0.01M phosphate buffer solution containing 5% normal rabbit serum (NRS)/10% lactose/0.1M NaCl, pH 7.4 was prepared.

The thus prepared solution was spotted on a bat in 20 μl portions and lyophilized to prepare the dried reagent 46 (signal substance-electron mediator).

[4] Production of antigen-immobilized flow path member 47 (hapten-immobilized membrane: E2-6CMO-γG-immobilized porous cellulose-blended ester membrane)

An antigen-immobilized flow path 47 (hapten-immobilized membrane) was prepared by repeating the procedure of Example 4[4] except that the diameter of the round shaped porous membrane was reduced to 10 mm.

[5] Production of electrode member

The electrode member 22 used was the one schematically shown in FIG. 3.

The parameters of the electrode member 22 are as described below.

Electrode member 22

Diameter of the through hole 32 (inner diameter of the work electrode 38): 3.5 mm Outer diameter of the work electrode 38: 6.5 mm (i.e., width of the work electrode 38: 1.5 mm)

Inner diameter of the counter electrode (reference electrode) 34 on the upper surface: 3.5 mm Outer diameter of the counter electrode (reference electrode) 34: 7 mm

[6] Production of specific binding assay device

The thus produced members were assembled as described below to produce the specific binding assay device shown in FIG. 17.

First, the absorption member 43 having disposed thereon the seal member 43a (having a thickness of 25 μm and a diameter of 7 mm) was disposed on the bottom board 48 made of an acrylic resin. The antigen-immobilized flow path member 47 (hapten-immobilized membrane) was disposed on and in alignment with the absorption member 43.

The electrode member 22 was then disposed on the antigen-immobilized flow path member 47 with the side of the work electrode 38 in contact with the antigen-immobilized flow path member 47 such that the through hole 32 was in alignment with the antigen-immobilized flow path member 47.

Next, the second layer 45 was disposed on the electrode member 22 such that the through hole 32 was in alignment with the second layer 45. A seal member 45a of PET (having a thickness of 25 μm and a diameter of 8 mm) was adhered in the center of the upper surface of the second layer 45. The first layer 44 was then disposed on the second layer 45.

The top cover 49 made of an acrylic resin provided with the sample inlet port 49a of 2 mm in diameter was then disposed on the first layer 44 such that the sample inlet port 49a was in alignment with the through hole 32. The top cover 49 and the bottom board 48 were adjusted such that tapped holes on four corners of the top cover 49 were in alignment with those of the bottom board 48, and the top cover 49 was screwed onto the bottom board 48. The dried reagent 46 was located in the sample inlet port 49a. The specific binding assay device adapted for measuring the concentration of estradiol was thus produced. The schematic view of the specific binding assay device is shown in FIG. 17.

[7] Measurement of E2 in plasma

In the electrode member 22 of the thus produced specific binding assay device, the terminal 34a of the counter electrode 34 was connected to the terminal of the counter electrode (reference electrode) of the current-measuring circuit, and the terminal of the work electrode of the current-measuring circuit was connected to the terminal 38a of the work electrode 38. The data from the current-measuring circuit were transmitted to the computer for further data analysis through a data collection board, AT-MIO-16X manufactured by National Instrument.

E2 of standard concentrations was added to the plasma of a normal donor to prepare plasma samples with the E2 concentration of 1 ng/ml and 10 ng/ml.

Each 80 μl of plasma samples with E2 was introduced through the sample inlet port 49a of the acrylic top cover to the top cover 49 of the specific binding assay device.

After the introduction of the sample into the specific binding assay device, potential of the work electrode was adjusted to −150 mV in relation to the counter electrode (reference electrode), and the current value was recorded.

Results

When the compounds shown in Table 5 were used in the adducts, current values corresponding to the E2 concentration was observed as in the cases of Examples 4 and 5. It was thus demonstrated that such compounds may be used regardless of the arrangement of the reagents in the assay method exemplified above, and that such compounds are versatile hydrogen peroxide-retaining agents with little adverse effects on the assay principle. Further, the hydrogen peroxide-retaining agents of the present invention can be used appropriately in any assay method using hydrogen peroxide at least as an assay reagent, not being limited in the MEDIA assay device described above.

MERITS OF THE PRESENT INVENTION

As described above, an accurate, highly sensitive assay device convenient for use in the assay is realized in the present invention by the use of a highly stable hydrogen peroxide adduct having little adverse effect on the assay reaction for the source of the peroxide, illustratively the hydrogen peroxide. When the hydrogen peroxide adduct of the present invention is used within a specific binding analyzing device using MEDIA method, the adduct may realize the convenient assay at any site within the device.

We claim:

1. A process for generating peroxide in the course of an assay wherein at least hydrogen peroxide is used as an analysis reagent, wherein the improvement comprises the steps of:
   (1) preparing an adduct in a dry state of
      (a) at least one member selected from the group consisting of monocarboxylic acids represented by the following formula (1):

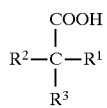

(1)

wherein $R^1$: H or $-CH_2-OH$;
$R^2$: H, $-NH_2$, $-OH$, or $-CH_2-OH$;

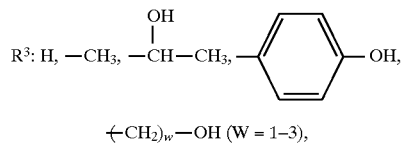

$-(CH_2)_w-OH$ (W = 1-3),

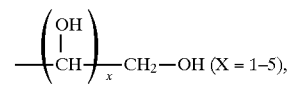

$-(CH_2)_y-NH-CO-NH_2$ (y = 0-3), or $-(CH_2)_z-NH-CO-CH_3$ (z = 0-3);

pyruvic acid, vanillic acid, picolinic acid and sodium and potassium salts thereof; and
      (b) hydrogen peroxide; and
   (2) adding an aqueous solution to said adduct in a dry state in the course of the analysis to thereby generate peroxide as an analysis reagent in the assay.

2. A process according to claim 1, wherein said monocarboxylic acid is at least one member selected from the group consisting of acetic acid, glycolic acid, propionic acid, 3-hydroxypropionic acid, 2,2-bis(hydroxymethyl) propionic acid, lactic acid, glyceric acid, gluconic acid, glucoheptonic acid, 4-hydroxyphenylacetic acid, hydantoic acid, citrulline, albizzin, serine, alanine, threonine, N-acetylglycine, pyruvic acid, vanillic acid, and picolinic acid.

3. A process for generating peroxide in the course of an assay wherein at least hydrogen peroxide is used as an analysis reagent, wherein the improvement comprises the steps of:
   (1) preparing an adduct in a dry state of
      (a) at least one member selected from the group consisting of an aliphatic dicarboxylic acid, an aromatic dicarboxylic acid, and sodium and potassium salts thereof; and
      (b) hydrogen peroxide; and
   (2) adding an aqueous solution to said adduct in a dry state in the course of the analysis to thereby generate peroxide as an analysis reagent in the assay.

4. A process according to claim 3, wherein said dicarboxylic acid is at least one member selected from the group consisting of oxalic acid, malonic acid, methylmalonic acid, succinic acid, oxaloacetic acid, methylsuccinic acid, 2,2-dimethysuccinic acid, maleic acid, fumalic acid, citraconic acid, acetylenedicarboxylic acid, malic acid, citramalic acid, tartaric acid, glutaric acid, diglycolic acid, 2-ketoglutaric acid, 3-ketoglutaric acid, 3-methylglutaric acid, 3-hydroxy-3-methylglutaric acid, adipic acid, mucic acid, pimelic acid, suberic acid, 1,2-cyclohexanedicarboxylic acid, 1,4-cyclohexanedicarboxylic acid, glutamic acid, N-(2-acetamid)iminodiacetic acid, o-phthalic acid, isophthalic acid, terephthalic acid, 4-hydroxyphthalic acid.

5. A process for generating peroxide in the course of an assay wherein at least hydrogen peroxide is used as an analysis reagent, wherein the improvement comprises the steps of:
   (1) preparing an adduct in a dry state of
      (a) at least one member selected from the group consisting of tricarboxylic acids represented by the following formula (2):

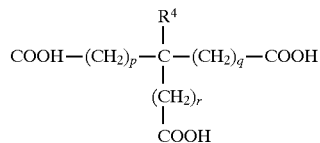

(2)

wherein $R^4$ is H or $-OH$, and p is 1 to 3, q is 0 to 3, and r is 0 to 3; and formula (3):

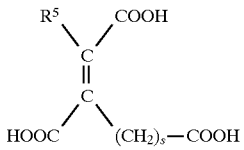

(3)

wherein $R^5$ is H or $CH_3$, and s is from 1 to 3; and sodium and potassium salts thereof; and
      (b) hydrogen peroxide; and
   (2) adding an aqueous solution to said adduct in a dry state in the course of the analysis to thereby generate peroxide as an analysis reagent in the assay.

6. A process according to claim 5, wherein said tricarboxylic acid is citric acid, aconit acid, or 1,3,5-pentatricarboxylic acid.

7. A process for generating peroxide in the course of an assay wherein at least hydrogen peroxide is used as an analysis reagent, wherein the improvement comprises the steps of:

(1) preparing an adduct in a dry state of
  (a) at least one member selected from the group consisting of tetracarboxylic acids represented by the following formula (4):

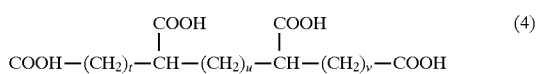

$$COOH-(CH_2)_t-CH-(CH_2)_u-CH-(CH_2)_v-COOH \quad (4)$$
$$\phantom{COOH-(CH_2)_t-}|\phantom{CH-(CH_2)_u-}|$$
$$\phantom{COOH-(CH_2)_t-}COOH \phantom{CH-(CH_2)_u}COOH$$

wherein t is from 0 to 3, u is from 0 to 3, and v is from 0 to 3;
  sodium and potassium salts thereof; and
  (b) hydrogen peroxide; and
(2) adding an aqueous solution to said adduct in a dry state in the course of the analysis to thereby generate peroxide as an analysis reagent in the assay.

8. A process according to claim 7, wherein said tetracarboxylic acid is butane-1,2,3,4-tetracarboxylic acid.

9. A process for generating peroxide in the course of an assay wherein at least hydrogen peroxide is used as an analysis reagent, wherein the improvement comprises the steps of:
  (1) preparing an adduct in a dry state of
    (a) at least one member selected from the group consisting of a uronic acid, a polyuronic acid, and sodium and potassium salts thereof; and
    (b) hydrogen peroxide; and
  (2) adding an aqueous solution to said adduct in a dry state in the course of the analysis to thereby generate peroxide as an analysis reagent in the assay.

10. A process according to claim 9, wherein said uronic acid is glucuronic acid, guluronic acid, mannuronic acid, galacturonic acid, or iduronic acid; and said polyuronic acid is arginic acid or pectic acid.

11. A process for generating peroxide in the course of an assay wherein at least hydrogen peroxide is used as an analysis reagent, wherein the improvement comprises the steps of:
  (1) preparing an adduct in a dry state of
    (a) at least one member selected from the group consisting of a phosphoric acid, and sodium and potassium salts thereof; and
    (b) hydrogen peroxide; and
  (2) adding an aqueous solution to said adduct in a dry state in the course of the analysis to thereby generate peroxide as an analysis reagent in the assay.

12. A process for generating peroxide in the course of an assay wherein at least hydrogen peroxide is used as an analysis reagent, wherein the improvement comprises the steps of:
  (1) preparing an adduct in a dry state of
    (a) at least one member selected from the group consisting of a hydroxyalkanesulfonic acid, aminoalkanesulfonic acid, hydroxybenzenesulfonic acid, and chondroitin sulfate, and sodium and potassium salts thereof; and
    (b) hydrogen peroxide; and
  (2) adding an aqueous solution to said adduct in a dry state in the course of the analysis to thereby generate peroxide as an analysis reagent in the assay.

13. A process according to claim 12, wherein said hydroxyalkanesulfonic acid is isethionic acid, said aminoalkanesulfonic acid is taurine or cysteic acid, and said hydroxybenzensulfonic acid is guaiacol sulfonic acid.

14. A process for generating peroxide in the course of an assay wherein at least hydrogen peroxide is used as an analysis reagent, wherein the improvement comprises the steps of:
  (1) preparing an adduct in a dry state of
    (a) at least one member selected from the group consisting of a monosaccharide, a disaccharide, a sugar alcohol, and polymers thereof; and
    (b) hydrogen peroxide; and
  (2) adding an aqueous solution to said adduct in a dry state in the course of the analysis to thereby generate peroxide as an analysis reagent in the assay.

15. A process according to claim 14, wherein said monsaccharide is a pentose, a hexose, or a heptose, said disaccahride is saccharose, maltose, lactose, or trehalose; said sugar alcohol is mannitol; and said polymer is dextrane or cellulose.

16. A process for generating peroxide in the course of an assay wherein at least hydrogen peroxide is used as an anaysis reagent, wherein the improvement comprises the steps of:
  (1) preparing an adduct in a dry state of
    (a) at least one member selected from the group consisting of a N-acetylglucosamine, ascorbic acid, creatinine, and polyethylene glycol; and
    (b) hydrogen peroxide; and
  (2) adding an aqueous solution to said adduct in a dry state in the course of the analysis to thereby generate peroxide as an analysis reagent in the assay.

17. A process for generating peroxide in the course of an assay wherein at least hydrogen peroxide is used as an analysis reagent, wherein the improvement comprises the steps of:
  (1) preparing an adduct in a dry state of
    (a) at least one member selected from the group consisting of a solid substance containing carboxyl group, phosphono group, sulfo group, and salts thereof; and
    (b) hydrogen peroxide; and
  (2) adding an aqueous solution to said adduct in a dry state in the course of the analysis to thereby generate peroxide as an analysis reagent in the assay.

* * * * *